United States Patent
Danilevskaya et al.

(10) Patent No.: US 9,701,975 B2
(45) Date of Patent: Jul. 11, 2017

(54) DOWN-REGULATION OF AUXIN RESPONSIVE GENES FOR IMPROVED PLANT PERFORMANCE

(71) Applicant: Pioneer Hi-Bred International, Inc., Johnston, IA (US)

(72) Inventors: Olga Nikolaevna Danilevskaya, Johnston, IA (US); Paulette Marie Gardner, Des Moines, IA (US); Guofu Li, Johnston, IA (US); Brooke Peterson-Burch, Ankeny, IA (US); Lisa I. Hagen, West Des Moines, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 9 days.

(21) Appl. No.: 14/422,806

(22) PCT Filed: Aug. 20, 2013

(86) PCT No.: PCT/US2013/055840
§ 371 (c)(1),
(2) Date: Feb. 20, 2015

(87) PCT Pub. No.: WO2014/031674
PCT Pub. Date: Feb. 27, 2014

(65) Prior Publication Data
US 2015/0240252 A1 Aug. 27, 2015

Related U.S. Application Data

(60) Provisional application No. 61/691,931, filed on Aug. 22, 2012.

(51) Int. Cl.
*C12N 15/82* (2006.01)
*C07K 14/415* (2006.01)

(52) U.S. Cl.
CPC ........ *C12N 15/8218* (2013.01); *C07K 14/415* (2013.01); *C12N 15/8261* (2013.01); *C12N 15/8273* (2013.01)

(58) Field of Classification Search
None
See application file for complete search history.

(56) References Cited

U.S. PATENT DOCUMENTS 9,089,610 B2 * 7/2015 McManus ........ A61K 47/48092

FOREIGN PATENT DOCUMENTS

| WO | 2008061240 A2 | 5/2008 |
| WO | 2011036160 A1 | 3/2011 |
| WO | 2011141499 A1 | 11/2011 |

OTHER PUBLICATIONS

Spartz et al., The Plant Journal, Feb. 2012, vol. 70, No. 6, pp. 978-990.*
Li et al, Scientific Reports 5, Article No. 12477, Jul. 24, 2015.*
Chen et al., J. Integr Plant Biol, Feb. 2014, vol. 56, No. 2, pp. 133-150, (abstract only).*
GenBank Accession No. EU968722.1, Zea mays clone 323704 SAUR33, Dec. 10, 2008, in body of action.*
GenBank Accession No. EU957904.1, Zea mays clone 1632067 SAUR52, Dec. 10, 2008.*
GenBank Accession No. NM_001157688.1, Zea mays clone 1632067 SAUR55, Apr. 10, 2009, in body of action.*
Knauss, et al.; "The Auxin-induced Maize Gene ZmSAUR2 Encodes a Short-lived Nuclear Protein Expressed in Elongating Tissues", The Journal of Biological Chemistry (2003) 278(26):23936-23943.
Yang, et al.; "Molecular and Biochemical Evidence for the Involvement of Calcium/Calmodulin in Auxin Action", The Journal of Biological Chemistry (2000) 275(5) 3137-3143.
Database EMBL: BI542465; "Maize ESTs from various cDNA libraries sequenced at Stanford University" Sep. 6, 2001.

* cited by examiner

*Primary Examiner* — Eileen O Hara
(74) *Attorney, Agent, or Firm* — Pioneer Hi-Bred Intl Inc.

(57) ABSTRACT

Methods for modulating plants using optimized ZmSAUR down-regulation constructs are disclosed. Also disclosed are nucleotide sequences, constructs, vectors, and modified plant cells, as well as transgenic plants displaying increased seed and/or biomass yield, improved tolerance to abiotic stress such as drought or high plant density, improved nitrogen utilization efficiency, increased ear tissue growth or kernel number.

3 Claims, No Drawings

SEQUENCE LISTING

```
<160> NUMBER OF SEQ ID NOS: 44

<210> SEQ ID NO 1
<211> LENGTH: 402
<212> TYPE: DNA
<213> ORGANISM: Zea mays

<400> SEQUENCE: 1
atggcgaagg gcgggctgag caagctccgg tgcatgatca agaggtggca ctcgtcgagc      60
cgcatcgtct cccgcgcccc gtcgccatca tcagcccacg acggcgccac ctccggcgac     120
gcgcactgcg cctcgttcca cggcgcggac gaggtgccca agggcctcca cccggtctac     180
gtcggcaagt cgcgccgccg gtacctcgtc gccgaggagc tcgtgggcca cccgctattc     240
cagaccctcg tccaccgcac cggcggcacc accgggggag cggcagcagg caccgtcgtc     300
ggctgcgagg tcgtcctctt cgagcacctc ctctggatgc tggagaacgc cgacccgcag     360
ccggagtccc tcgacgagct ggtcgactac tacgcttgct ga                       402

<210> SEQ ID NO 2
<211> LENGTH: 133
<212> TYPE: PRT
<213> ORGANISM: Zea mays

<400> SEQUENCE: 2

Met Ala Lys Gly Gly Leu Ser Lys Leu Arg Cys Met Ile Lys Arg Trp
1               5                   10                  15

His Ser Ser Arg Ile Val Ser Arg Ala Pro Ser Pro Ser Ser Ala
            20                  25                  30

His Asp Gly Ala Thr Ser Gly Asp Ala His Cys Ala Ser Phe His Gly
        35                  40                  45
```

```
Ala Asp Glu Val Pro Lys Gly Leu His Pro Val Tyr Val Gly Lys Ser
    50                  55                  60

Arg Arg Arg Tyr Leu Val Ala Glu Glu Leu Val Gly His Pro Leu Phe
65                  70                  75                  80

Gln Thr Leu Val His Arg Thr Gly Thr Thr Gly Gly Ala Ala Ala
                85                  90                  95

Gly Thr Val Val Gly Cys Glu Val Val Leu Phe Glu His Leu Leu Trp
                100                 105                 110

Met Leu Glu Asn Ala Asp Pro Gln Pro Glu Ser Leu Asp Glu Leu Val
                115                 120                 125

Asp Tyr Tyr Ala Cys
                130

<210> SEQ ID NO 3
<211> LENGTH: 459
<212> TYPE: DNA
<213> ORGANISM: Zea mays

<400> SEQUENCE: 3
atgatcagcg ccaagaagat tgctcatctc gccaagaagt ggcagaggat ggctgcacaa      60
gggaggaagc gcctcgcctt gggggcggca gcaaagcaag ccgacgagtg ctgcagctat     120
gtggcgagca agggccactg cgcggtgtac acggccgacg ggcacggtt cgaggtgccg      180 ctggcgtgcc ttagcacccc ggtcttcggg gagctcctac aaatgtcaca ggaggagttc     240
ggcttcacgg gcggcgatgg caggatcacg ctgccctgcg acgcggcgat catggagtac     300
gccatgtgtt tgctcaggag aggagcctct gctgagctag agcaggcgtt ccttagcacc     360
atggccatgt catgccactg tgccagccac atggcgccgt atgttggacg agctcacgag     420
ccagacagca gattgttgtt tagtttctgt tcagtgtag                            459

<210> SEQ ID NO 4
<211> LENGTH: 152
<212> TYPE: PRT
<213> ORGANISM: Zea mays

<400> SEQUENCE: 4

Met Ile Ser Ala Lys Lys Ile Ala His Leu Ala Lys Lys Trp Gln Arg
1               5                   10                  15

Met Ala Ala Gln Gly Arg Lys Arg Leu Ala Leu Gly Ala Ala Ala Lys
                20                  25                  30

Gln Ala Asp Glu Cys Cys Ser Tyr Val Ala Ser Lys Gly His Cys Ala
            35                  40                  45

Val Tyr Thr Ala Asp Gly Ala Arg Phe Glu Val Pro Leu Ala Cys Leu
    50                  55                  60

Ser Thr Pro Val Phe Gly Glu Leu Leu Gln Met Ser Gln Glu Glu Phe
65                  70                  75                  80

Gly Phe Thr Gly Gly Asp Gly Arg Ile Thr Leu Pro Cys Asp Ala Ala
                85                  90                  95

Ile Met Glu Tyr Ala Met Cys Leu Leu Arg Arg Gly Ala Ser Ala Glu
                100                 105                 110

Leu Glu Gln Ala Phe Leu Ser Thr Met Ala Met Ser Cys His Cys Ala
                115                 120                 125

Ser His Met Ala Pro Tyr Val Gly Arg Ala His Glu Pro Asp Ser Arg
            130                 135                 140

Leu Leu Phe Ser Phe Cys Ser Val
145                 150
```

<210> SEQ ID NO 5
<211> LENGTH: 477
<212> TYPE: DNA
<213> ORGANISM: Zea mays

<400> SEQUENCE: 5

```
atggtcagcg ccaagagact tgtgcaaatg gccaagaagt ggcagaggat ggccgccacg    60
gcaaggaggc ggatcgcact ggcgccgccg gcaaaaggag ccgccgaggg atcgtcgccg   120
ccgtgcagca cctcgcgtgt agctgtagcc ggcaagggcc actgcgtggt gtactcggcg   180
gacggcaggc ggttcgaggt cccgctgccg tacctcgaca ccgccgtctt cggcgtgctc   240
ctcggcatgt cgcgggagga gttcgggttc gccggtggcg acggcaggat cacggtgccc   300
tgtgacgccg ccgtcatgga gtacgtcatg tgtttgcttc ggagagacgc gtcggaagag   360
gtggtgaggg cgttcctgag ctccgtggtg agccggcctt gcagccactg tggaaatggc   420
tcgctggtgc agtccaccac gggagttcgc cagcaagctg ctgtttctag cttctga      477
```

<210> SEQ ID NO 6
<211> LENGTH: 158
<212> TYPE: PRT
<213> ORGANISM: Zea mays

<400> SEQUENCE: 6

```
Met Val Ser Ala Lys Arg Leu Val Gln Met Ala Lys Lys Trp Gln Arg
1               5                   10                  15
Met Ala Ala Thr Ala Arg Arg Arg Ile Ala Leu Ala Pro Pro Ala Lys
            20                  25                  30
Gly Ala Ala Glu Gly Ser Ser Pro Pro Cys Ser Thr Ser Arg Val Ala
        35                  40                  45
Val Ala Gly Lys Gly His Cys Val Val Tyr Ser Ala Asp Gly Arg Arg
    50                  55                  60
Phe Glu Val Pro Leu Pro Tyr Leu Asp Thr Ala Val Phe Gly Val Leu
65                  70                  75                  80
Leu Gly Met Ser Arg Glu Glu Phe Gly Phe Ala Gly Gly Asp Gly Arg
                85                  90                  95
Ile Thr Val Pro Cys Asp Ala Ala Val Met Glu Tyr Val Met Cys Leu
            100                 105                 110
Leu Arg Arg Asp Ala Ser Glu Glu Val Val Arg Ala Phe Leu Ser Ser
        115                 120                 125
Val Val Ser Arg Pro Cys Ser His Cys Gly Asn Gly Ser Leu Val Gln
    130                 135                 140
Ser Thr Thr Gly Val Arg Gln Gln Ala Ala Val Ser Ser Phe
145                 150                 155
```

<210> SEQ ID NO 7
<211> LENGTH: 435
<212> TYPE: DNA
<213> ORGANISM: Glycine max

<400> SEQUENCE: 7

```
atggcagcaa gcatagccgc caccacagca gcagcgccgt cgccgatgac gagtcctcct    60
ccagatcaga cctccacgcc gtctacgtcg gcaagtcccg ccgcctctat cgcgtctcct   120
ccgacgttgt cgaccacccc gtcttccggg aactcgtcga gagatcccgc gattctgacc   180
aacaacaaaa cgaagacact actacgatca atgtcgtcgc atgcgaggtt gtccttttcg   240
```

```
aacacttgct ctggatgctc gataacgccg acccacaacc cgagtcactc aacgaactcg    300
tcgacttcta cggttgctaa tgctagctac tatctatccc ataccttcca cgtgtcccta    360
tcatcccaca ttattaaaaa aaacacgtat attatattat accacttccg attaattttt    420
ataagaaaca agtaa                                                     435
```

<210> SEQ ID NO 8
<211> LENGTH: 143
<212> TYPE: PRT
<213> ORGANISM: Glycine max

<400> SEQUENCE: 8

```
Met Ala Ala Ser Ile Ala Ala Thr Thr Ala Ala Pro Ser Pro Met
1               5                   10                  15

Thr Ser Pro Pro Pro Asp Gln Thr Ser Thr Pro Ser Thr Ser Ala Ser
                20                  25                  30

Pro Ala Ala Ser Ile Ala Ser Pro Pro Thr Leu Ser Thr Thr Pro Ser
            35                  40                  45

Ser Gly Asn Ser Ser Arg Asp Pro Ala Ile Thr Asn Asn Lys Thr Lys
    50                  55                  60

Thr Leu Leu Arg Ser Met Ser Ser His Ala Arg Leu Ser Phe Ser Asn
65                  70                  75                  80

Thr Cys Ser Gly Cys Ser Ile Thr Pro Thr His Asn Pro Ser His Ser
                85                  90                  95

Thr Asn Ser Ser Thr Ser Thr Val Ala Asn Ala Ser Tyr Tyr Leu Ser
                100                 105                 110

His Thr Phe His Val Ser Leu Ser Ser His Ile Ile Lys Lys Asn Thr
            115                 120                 125

Tyr Ile Ile Leu Tyr His Phe Arg Leu Ile Phe Ile Arg Asn Lys
        130                 135                 140
```

<210> SEQ ID NO 9
<211> LENGTH: 339
<212> TYPE: DNA
<213> ORGANISM: Glycine max

<400> SEQUENCE: 9

```
atgatcagcg caaatagact cattgaaatg gcaagaaagt ggcagaaaat ggcagtggga     60
aatcgcaaga gaatttcata cccaccaagg aaccataata ataatgttca tatgcattat    120
tcatccacag ccaataaggg acacttcgtt gtttacagcg tcgatcataa gcgattcgag    180
gttcccctta gtaccttag cacgaacgtg ttcagagagc tactgaattg gtccgaagag    240
gagtttgggt taccttccaa tggacctatt acgctgcctt gtgatagcgt gttcttggac    300
tacgtaatct cgttaattcg agaacgcgtt cctgaagaa                           339
```

<210> SEQ ID NO 10
<211> LENGTH: 113
<212> TYPE: PRT
<213> ORGANISM: Glycine max

<400> SEQUENCE: 10

```
Met Ile Ser Ala Asn Arg Leu Ile Glu Met Ala Arg Lys Trp Gln Lys
1               5                   10                  15

Met Ala Val Gly Asn Arg Lys Arg Ile Ser Tyr Pro Pro Arg Asn His
                20                  25                  30

Asn Asn Asn Val His Met His Tyr Ser Ser Thr Ala Asn Lys Gly His
            35                  40                  45
```

Phe Val Val Tyr Ser Val Asp His Lys Arg Phe Glu Val Pro Leu Lys
            50                  55                  60

Tyr Leu Ser Thr Asn Val Phe Arg Glu Leu Leu Asn Trp Ser Glu Glu
 65                  70                  75                  80

Glu Phe Gly Leu Pro Ser Asn Gly Pro Ile Thr Leu Pro Cys Asp Ser
                 85                  90                  95

Val Phe Leu Asp Tyr Val Ile Ser Leu Ile Arg Glu Arg Val Pro Glu
                100                 105                 110

Glu

<210> SEQ ID NO 11
<211> LENGTH: 426
<212> TYPE: DNA
<213> ORGANISM: Glycine max

<400> SEQUENCE: 11
atgattagtt ccaaaaagat catccaaatg gcttggaagt ggcagaaaga ggtgacaaat      60
taccaaatga agagaatcct atggccaaag actcaagaaa atgtagcaaa agcagagaag     120
aagggtcact tgttgtgta tagctcagat aagaggcgct ttgtgcttcc tttgctgtat     180
ttgaacaaca aaatcttcag ggagcttttc aaattggcag aagaggagtt tggtctctct     240
agcaacgtgc ccctaacgtt gccatgtgaa gccacgttaa tagagtacgt aataacgttg     300
atccagagaa acgtaactaa ggatctggag gaagctgtgt taatgttcgt agctactagt     360
cgatgccaat cgcatgttga tcttcatcgt gaacgaacca atcaacattt gctttgcagc     420
tattaa                                                                426

<210> SEQ ID NO 12
<211> LENGTH: 141
<212> TYPE: PRT
<213> ORGANISM: Glycine max

<400> SEQUENCE: 12

Met Ile Ser Ser Lys Lys Ile Ile Gln Met Ala Trp Lys Trp Gln Lys
 1               5                  10                  15

Glu Val Thr Asn Tyr Gln Met Lys Arg Ile Leu Trp Pro Lys Thr Gln
                20                  25                  30

Glu Asn Val Ala Lys Ala Glu Lys Lys Gly His Phe Val Val Tyr Ser
             35                  40                  45

Ser Asp Lys Arg Arg Phe Val Leu Pro Leu Leu Tyr Leu Asn Asn Lys
         50                  55                  60

Ile Phe Arg Glu Leu Phe Lys Leu Ala Glu Glu Glu Phe Gly Leu Ser
 65                  70                  75                  80

Ser Asn Val Pro Leu Thr Leu Pro Cys Glu Ala Thr Leu Ile Glu Tyr
                 85                  90                  95

Val Ile Thr Leu Ile Gln Arg Asn Val Thr Lys Asp Leu Glu Glu Ala
                100                 105                 110

Val Leu Met Phe Val Ala Thr Ser Arg Cys Gln Ser His Val Asp Leu
            115                 120                 125

His Arg Glu Arg Thr Asn Gln His Leu Leu Cys Ser Tyr
        130                 135                 140

<210> SEQ ID NO 13
<211> LENGTH: 366
<212> TYPE: DNA
<213> ORGANISM: Glycine max

<400> SEQUENCE: 13

```
atgtccaaag caggaaaact aacgaagctc aagtcagtgc tgaggaaatg gaactcattc      60
agcaacaaac acagtcaagt cagtgtcatc tccgccgtcg cgaacgacgg aggtgacacc     120
tcatcgctcc tcccagtgta tgttggggagg acacgtcggc gttatctcgt gagcgccgat    180
gtagtcggac acccgctctt cagggagctg gtaggccggt cccgcgacgg ctccaaggag    240
gaggacgagg acaccatcaa cgtggcgtgc gaggttgtcc tattcgagca cttgctctgg    300
atgctccaca tgccgatcc tcaacccgag tcgctcgatg aactcgccga tttttacgcc      360
tgctag                                                                366
```

<210> SEQ ID NO 14
<211> LENGTH: 121
<212> TYPE: PRT
<213> ORGANISM: Glycine max

<400> SEQUENCE: 14

```
Met Ser Lys Ala Gly Lys Leu Thr Lys Leu Lys Ser Val Leu Arg Lys
1               5                   10                  15
Trp Asn Ser Phe Ser Asn Lys His Ser Gln Val Ser Val Ile Ser Ala
            20                  25                  30
Val Ala Asn Asp Gly Gly Asp Thr Ser Ser Leu Leu Pro Val Tyr Val
        35                  40                  45
Gly Arg Thr Arg Arg Tyr Leu Val Ser Ala Asp Val Val Gly His
    50                  55                  60
Pro Leu Phe Arg Glu Leu Val Gly Arg Ser Arg Asp Gly Ser Lys Glu
65                  70                  75                  80
Glu Asp Glu Asp Thr Ile Asn Val Ala Cys Glu Val Val Leu Phe Glu
                85                  90                  95
His Leu Leu Trp Met Leu His Asn Ala Asp Pro Gln Pro Glu Ser Leu
            100                 105                 110
Asp Glu Leu Ala Asp Phe Tyr Ala Cys
        115                 120
```

<210> SEQ ID NO 15
<211> LENGTH: 384
<212> TYPE: DNA
<213> ORGANISM: Glycine max

<400> SEQUENCE: 15

```
atggcaagag gtggaaaact aacgaagcta aagtcagtgc tgaagaaatg gaactcattc      60
ggcaacaaca gcaagcatag ccgccaccac agcatcagcg ccgtcgcaga cgacgaatcc    120
tcctccagat cagacctcca cgccgtctac gtcggcaagt cccgccgcct ctaccgcgtc    180
gcctccgacg tcgtcgacca ccccgtcttc cgggaactcg tcgagagatc ccgcgactcc    240
gaccaacaac aacaaagcga agacaccact atcaatgtcg tcgcatgtga ggttgtcctt    300
ttcgaacact tgctctggat gctcgataac gccgacccac aacccgagtc actcaacgaa    360
ctcgtcgact tctacgcttg ctaa                                            384
```

<210> SEQ ID NO 16
<211> LENGTH: 127
<212> TYPE: PRT
<213> ORGANISM: Glycine max

<400> SEQUENCE: 16

Met Ala Arg Gly Gly Lys Leu Thr Lys Leu Lys Ser Val Leu Lys Lys
1               5                   10                  15

Trp Asn Ser Phe Gly Asn Asn Ser Lys His Ser Arg His His Ser Ile
            20                  25                  30

Ser Ala Val Ala Asp Asp Glu Ser Ser Arg Ser Asp Leu His Ala
            35                  40                  45

Val Tyr Val Gly Lys Ser Arg Arg Leu Tyr Arg Val Ala Ser Asp Val
        50                  55                  60

Val Asp His Pro Val Phe Arg Glu Leu Val Glu Arg Ser Arg Asp Ser
65                  70                  75                  80

Asp Gln Gln Gln Ser Glu Asp Thr Thr Ile Asn Val Val Ala Cys
                85                  90                  95

Glu Val Val Leu Phe Glu His Leu Leu Trp Met Leu Asp Asn Ala Asp
                100                 105                 110

Pro Gln Pro Glu Ser Leu Asn Glu Leu Val Asp Phe Tyr Ala Cys
            115                 120                 125

<210> SEQ ID NO 17
<211> LENGTH: 402
<212> TYPE: DNA
<213> ORGANISM: Oryza sativa

<400> SEQUENCE: 17
atggggaagg gaggcgggct gagcaagctg aggtgcatga tcaggaggtg gcactcgtcg      60
agccgcatcg cgcgggcgcc gccgtcggcg ggggagctgg aggagggctc tgcggcggcg     120
gcggggaggg cggcgtcgtt ccacggcgcg gacgaggtgc ccaagggct ccacccggtg     180 tacgtcggca gtcgcggcg gcggtacctc atcgccgagg agctcgtcgg ccacccgctg     240
ttccagaacc tcgtcgaccg caccggcggc ggcggcggcg gcggcgccgc gaccgtcgtc     300
ggctgcgagg tcgtgctgtt cgagcacctg ctctggatgc tggagaacgc cgacccgcag     360
ccggagtccc tcgacgagct cgtcgagtac tacgcctgct ga                       402

<210> SEQ ID NO 18
<211> LENGTH: 133
<212> TYPE: PRT
<213> ORGANISM: Oryza sativa

<400> SEQUENCE: 18

Met Gly Lys Gly Gly Gly Leu Ser Lys Leu Arg Cys Met Ile Arg Arg
1               5                   10                  15

Trp His Ser Ser Ser Arg Ile Ala Arg Ala Pro Pro Ser Ala Gly Glu
            20                  25                  30

Leu Glu Glu Gly Ser Ala Ala Ala Ala Gly Arg Ala Ala Ser Phe His
        35                  40                  45

Gly Ala Asp Glu Val Pro Lys Gly Leu His Pro Val Tyr Val Gly Lys
    50                  55                  60

Ser Arg Arg Arg Tyr Leu Ile Ala Glu Glu Leu Val Gly His Pro Leu
65                  70                  75                  80

Phe Gln Asn Leu Val Asp Arg Thr Gly Gly Gly Gly Gly Gly Ala
                85                  90                  95

Ala Thr Val Val Gly Cys Glu Val Val Leu Phe Glu His Leu Leu Trp
                100                 105                 110

Met Leu Glu Asn Ala Asp Pro Gln Pro Glu Ser Leu Asp Glu Leu Val
            115                 120                 125

Glu Tyr Tyr Ala Cys

-continued

```
                  130
```

<210> SEQ ID NO 19
<211> LENGTH: 426
<212> TYPE: DNA
<213> ORGANISM: Oryza sativa

<400> SEQUENCE: 19

```
atgatcagtg ccaggagagt tgctcagctg gccaagaagt ggcagaggat ggcagcactc    60
ggaaggaaga ggctcacagt gagagccaaa caagatcaag aatgctgcag ttccatggca   120
ggcaagggcc actgcgccat gtacacggcg gacgggagcc gattcgaggt cccgttggcg   180
tacctcggca cggcggtctt cagtgagctc ctccggatgt cacaggagga gtttggtttc   240
tcgatcgatg caggatcat gctgccttgt gatgctgctg tgatggagta tgccatgtgc    300
ttgctcagga gaaatgcttc ggttgaggtg agaaagcat tgctgagctc catggtggca    360
tcttgccact acactggttc tatggtgcca actgttggag tcaatcagca aatttcctgc   420
ttgtag                                                              426
```

<210> SEQ ID NO 20
<211> LENGTH: 141
<212> TYPE: PRT
<213> ORGANISM: Oryza sativa

<400> SEQUENCE: 20

```
Met Ile Ser Ala Arg Arg Val Ala Gln Leu Ala Lys Lys Trp Gln Arg
1               5                  10                  15

Met Ala Ala Leu Gly Arg Lys Arg Leu Thr Val Arg Ala Lys Gln Asp
            20                  25                  30

Gln Glu Cys Cys Ser Ser Met Ala Gly Lys Gly His Cys Ala Met Tyr
        35                  40                  45

Thr Ala Asp Gly Ser Arg Phe Glu Val Pro Leu Ala Tyr Leu Gly Thr
    50                  55                  60

Ala Val Phe Ser Glu Leu Leu Arg Met Ser Gln Glu Glu Phe Gly Phe
65                  70                  75                  80

Ser Ile Asp Gly Arg Ile Met Leu Pro Cys Asp Ala Ala Val Met Glu
                85                  90                  95

Tyr Ala Met Cys Leu Leu Arg Arg Asn Ala Ser Val Glu Val Glu Lys
            100                 105                 110

Ala Leu Leu Ser Ser Met Val Ala Ser Cys His Tyr Thr Gly Ser Met
        115                 120                 125

Val Pro Thr Val Gly Val Asn Gln Gln Ile Ser Cys Leu
    130                 135                 140
```

<210> SEQ ID NO 21
<211> LENGTH: 453
<212> TYPE: DNA
<213> ORGANISM: Oryza sativa

<400> SEQUENCE: 21

```
atggccatga tcagcgccaa gaggattgct cagctagcaa agaaatggcg aaggatggca    60
gcactgggga ggaagaggct tacaatgtcg tcgacggcga tggcgacgga agaagcccaa   120
ggttgctcca cggcggtggc cggcaagggt cactgcgcca tctacaccgc cgacggcgcg   180
cggttcgagg tgccattggc gtacctcggc acgcgggtct tggcgagctc cctgaccatg   240
tctcgggagg agtacggctt ctccggcgac ggcaagatca cgctgccgtg tgacgccatg   300
```

```
gtgatggagt acgtgttgtg cttgctcgga agaaacgctt cggcagaggt tgagaaggcg    360
ttcttgagct ccatggtgat gccgtgccac tatgcaagct gtgtgacacc atctctggga    420
gcttgtcagc aagttgctgt ttgcagtaac tag                                  453

<210> SEQ ID NO 22
<211> LENGTH: 150
<212> TYPE: PRT
<213> ORGANISM: Oryza sativa

<400> SEQUENCE: 22

Met Ala Met Ile Ser Ala Lys Arg Ile Ala Gln Leu Ala Lys Lys Trp
1               5                   10                  15

Arg Arg Met Ala Ala Leu Gly Arg Lys Arg Leu Thr Met Ser Ser Thr
            20                  25                  30

Ala Met Ala Thr Glu Glu Ala Gln Gly Cys Ser Thr Ala Val Ala Gly
        35                  40                  45

Lys Gly His Cys Ala Ile Tyr Thr Ala Asp Gly Ala Arg Phe Glu Val
    50                  55                  60

Pro Leu Ala Tyr Leu Gly Thr Ala Val Leu Gly Glu Leu Leu Thr Met
65                  70                  75                  80

Ser Arg Glu Glu Tyr Gly Phe Ser Gly Asp Gly Lys Ile Thr Leu Pro
                85                  90                  95

Cys Asp Ala Met Val Met Glu Tyr Val Leu Cys Leu Leu Gly Arg Asn
            100                 105                 110

Ala Ser Ala Glu Val Glu Lys Ala Phe Leu Ser Ser Met Val Met Pro
        115                 120                 125

Cys His Tyr Ala Ser Cys Val Thr Pro Ser Leu Gly Ala Cys Gln Gln
    130                 135                 140

Val Ala Val Cys Ser Asn
145                 150

<210> SEQ ID NO 23
<211> LENGTH: 420
<212> TYPE: DNA
<213> ORGANISM: Sorghum bicolor

<400> SEQUENCE: 23
atggcgaaga gcgggctgag caagctccgg tgcatgatca agaggtggca ctcgtcgagc    60
cgcatcgtct cccgcgcgcc gccgtcgcca tcggctcacg accacgacgg ccacgacggc    120
ggcggcgaca tcatctccgg cgacgcgcag ggcgcgtcgt tccacggcgc ggacgaggtg    180
cccaagggcc tgcacccggt ctacgtcggc aagtcgcgcc gccggtacct catcgccgag    240
gacctcgtgg ccacccgct gttccagacc ctcgtccacc gcaccggcgg agcggcagga    300
ccaggcaccg tcgtcgtcgg ctgcgaggtc gtgctgttcg agcacctcct ctggatgctg    360
gagaacgccg acccgcagcc ggagtccctc gacgagctcg tcgactacta cgcgtgctga   420

<210> SEQ ID NO 24
<211> LENGTH: 139
<212> TYPE: PRT
<213> ORGANISM: Sorghum bicolor

<400> SEQUENCE: 24

Met Ala Lys Ser Gly Leu Ser Lys Leu Arg Cys Met Ile Lys Arg Trp
1               5                   10                  15

His Ser Ser Ser Arg Ile Val Ser Arg Ala Pro Pro Ser Pro Ser Ala
            20                  25                  30
```

```
His Asp His Asp Gly His Asp Gly Gly Gly Asp Ile Ile Ser Gly Asp
     35                  40                  45

Ala Gln Gly Ala Ser Phe His Gly Ala Asp Glu Val Pro Lys Gly Leu
 50                  55                  60

His Pro Val Tyr Val Gly Lys Ser Arg Arg Tyr Leu Ile Ala Glu
 65                  70                  75                  80

Asp Leu Val Gly His Pro Leu Phe Gln Thr Leu Val His Arg Thr Gly
                 85                  90                  95

Gly Ala Ala Gly Pro Gly Thr Val Val Gly Cys Glu Val Val Leu
                100                 105                 110

Phe Glu His Leu Leu Trp Met Leu Glu Asn Ala Asp Pro Gln Pro Glu
            115                 120                 125

Ser Leu Asp Glu Leu Val Asp Tyr Tyr Ala Cys
        130                 135
```

```
<210> SEQ ID NO 25
<211> LENGTH: 432
<212> TYPE: DNA
<213> ORGANISM: Sorghum bicolor

<400> SEQUENCE: 25
atgatcagcg ccaagatgat tgctcatctg gccaagaagt ggcagaggat ggctgcacaa    60
ggcaggaagc gcctcaccctg ggctgcagca gcaaaggaag ccaacgagtg ctggagctcc   120
gtggcgagca agggccactg cacggtgtac acggccgacg gcgcgcggtt cgaggtgccg   180
ctggcgtgcc ttagcaccgc gttcttccgg gagctcctgc aaatgtcaca ggaagagttc   240
gggttcacgg gcggcgatgg caggatcaca cttccctgcg acgcggccgt catggagtac   300
gccatgtgtt tgctcaggag aggcgcctct gccgagctag agcaggcttt ccttagcacc   360
atggcgatgt cgtgccacta tgtcagccgt gtggcgccgt gtattgaagc aagccagcag   420
attgctgttt ag                                                       432
```

```
<210> SEQ ID NO 26
<211> LENGTH: 143
<212> TYPE: PRT
<213> ORGANISM: Sorghum bicolor

<400> SEQUENCE: 26

Met Ile Ser Ala Lys Met Ile Ala His Leu Ala Lys Lys Trp Gln Arg
 1               5                  10                  15

Met Ala Ala Gln Gly Arg Lys Arg Leu Thr Trp Ala Ala Ala Ala Lys
                 20                  25                  30

Glu Ala Asn Glu Cys Trp Ser Ser Val Ala Ser Lys Gly His Cys Thr
             35                  40                  45

Val Tyr Thr Ala Asp Gly Ala Arg Phe Glu Val Pro Leu Ala Cys Leu
 50                  55                  60

Ser Thr Ala Phe Phe Arg Glu Leu Leu Gln Met Ser Gln Glu Glu Phe
 65                  70                  75                  80

Gly Phe Thr Gly Gly Asp Gly Arg Ile Thr Leu Pro Cys Asp Ala Ala
                 85                  90                  95

Val Met Glu Tyr Ala Met Cys Leu Leu Arg Arg Gly Ala Ser Ala Glu
            100                 105                 110

Leu Glu Gln Ala Phe Leu Ser Thr Met Ala Met Ser Cys His Tyr Val
            115                 120                 125

Ser Arg Val Ala Pro Cys Ile Glu Ala Ser Gln Gln Ile Ala Val
```

<210> SEQ ID NO 27
<211> LENGTH: 444
<212> TYPE: DNA
<213> ORGANISM: Sorghum bicolor

<400> SEQUENCE: 27

```
atggtcagcg ccaagagact tgctcaaatg gcaaagaagt ggcaaagaat ggcggccatg      60
gcaaggaggc ggatcgcatc ggcgccgacc aaaggaacca ccgagggatc atcaccgtgc     120
agcacttcgc cggtggccgg caaaggccac tgcgtggtgt actcggcaga cggcaggcga     180
ttcgaggtcc cgctggcgta cctcgacacc gccatctttg gcgtgctcct cagcatgtcg     240
caggaggagt tcgggtttgc cagcgacgat ggcaggatca tggtgccgtg tgatgccgcc     300
gtcatggagt acgtgatgtg tttgcttagg agagatgcat cggaagaggt ggtgagggcg     360
ttcctcagct ccatggtgag gccttgccac tgtggaaatg gcttggtgca atccatggga     420
gttagccagc aagctgtgtt ctag                                            444
```

<210> SEQ ID NO 28
<211> LENGTH: 147
<212> TYPE: PRT
<213> ORGANISM: Sorghum bicolor

<400> SEQUENCE: 28

```
Met Val Ser Ala Lys Arg Leu Ala Gln Met Ala Lys Lys Trp Gln Arg
1               5                   10                  15
Met Ala Ala Met Ala Arg Arg Arg Ile Ala Ser Ala Pro Thr Lys Gly
            20                  25                  30
Thr Thr Glu Gly Ser Ser Pro Cys Ser Thr Ser Pro Val Ala Gly Lys
        35                  40                  45
Gly His Cys Val Val Tyr Ser Ala Asp Gly Arg Arg Phe Glu Val Pro
    50                  55                  60
Leu Ala Tyr Leu Asp Thr Ala Ile Phe Gly Val Leu Leu Ser Met Ser
65                  70                  75                  80
Gln Glu Glu Phe Gly Phe Ala Ser Asp Asp Gly Arg Ile Met Val Pro
                85                  90                  95
Cys Asp Ala Ala Val Met Glu Tyr Val Met Cys Leu Leu Arg Arg Asp
            100                 105                 110
Ala Ser Glu Glu Val Val Arg Ala Phe Leu Ser Ser Met Val Arg Pro
        115                 120                 125
Cys His Cys Gly Asn Gly Leu Val Gln Ser Met Gly Val Ser Gln Gln
    130                 135                 140
Ala Val Phe
145
```

<210> SEQ ID NO 29
<211> LENGTH: 36
<212> TYPE: DNA
<213> ORGANISM: Artificial sequence
<220> FEATURE:
<223> OTHER INFORMATION: primer

<400> SEQUENCE: 29

```
ttcgaaggat cctccggtgc atgatcaaga ggtggc                                36
```

<210> SEQ ID NO 30
<211> LENGTH: 27

```
<212> TYPE: DNA
<213> ORGANISM: Artificial sequence
<220> FEATURE:
<223> OTHER INFORMATION: primer

<400> SEQUENCE: 30
tcgtcctctt cgagccccgg ggtcgac                                        27

<210> SEQ ID NO 31
<211> LENGTH: 300
<212> TYPE: DNA
<213> ORGANISM: Zea mays

<400> SEQUENCE: 31
tccggtgcat gatcaagagg tggcactcgt cgagccgcat cgtctcccgc gccccgtcgc     60
catcatcagc ccacgacggc gccacctccg gcgacgcgca ctgcgcctcg ttccacggcg    120
cggacgaggt gcccaagggc ctccacccgg tctacgtcgg caagtcgcgc cgccggtacc    180
tcgtcgccga ggagctcgtg gccaccccgc tattccagac cctcgtccac cgcaccggcg    240
gcaccaccgg gggagcggca gcaggcaccg tcgtcggctg cgaggtcgtc ctcttcgagc    300

<210> SEQ ID NO 32
<211> LENGTH: 300
<212> TYPE: DNA
<213> ORGANISM: Zea mays

<400> SEQUENCE: 32
gctcgaagag gacgacctcg cagccgacga cggtgcctgc tgccgctccc ccggtggtgc     60
cgccggtgcg gtggacgagg gtctggaata gcgggtggcc cacgagctcc tcggcgacga    120
ggtaccggcg gcgcgacttg ccgacgtaga ccgggtggag gcccttgggc acctcgtccg    180
cgccgtggaa cgaggcgcag tgcgcgtcgc cggaggtggc cgtcgtgg gctgatgatg     240 gcgacggggc gcgggagacg atgcggctcg acgagtgcca cctcttgatc atgcaccgga    300

<210> SEQ ID NO 33
<211> LENGTH: 1022
<212> TYPE: DNA
<213> ORGANISM: Zea mays

<400> SEQUENCE: 33
tccggtgcat gatcaagagg tggcactcgt cgagccgcat cgtctcccgc gccccgtcgc     60
catcatcagc ccacgacggc gccacctccg gcgacgcgca ctgcgcctcg ttccacggcg    120
cggacgaggt gcccaagggc ctccacccgg tctacgtcgg caagtcgcgc cgccggtacc    180
tcgtcgccga ggagctcgtg gccaccccgc tattccagac cctcgtccac cgcaccggcg    240
gcaccaccgg gggagcggca gcaggcaccg tcgtcggctg cgaggtcgtc ctcttcgagc    300
cccggggtcg acctgcaggc ggccgcgaat tcactagtga ttctaactaa ctagaggtac    360
agtacacaca catatgtata tatgtatgat gtatcccttc gatcgaaggc atgccttggt    420 cgataactg agtagtcatt ttattacgtt atttttgacaa gtcagtagtt catccatttg    480
tcccattttt tcagctagga agtttggtta cactggcctt ggtctaataa ctgagtagtc    540
attttattac gttgtttcga caagtcagta gctcatccat ctgtcccatt ttttcagct    600 aggaagtttg gttacactgg acttggtcta ataactgagt agtcatttta ttacgttgtt    660
tcgacaagtc attagctcat ccatctgtcc cattttttcag ctctaactaa ctagatcccg    720
gggctcgaag aggacgacct cgcagccgac gacggtgcct gctgccgctc cccggtggt    780
```

-continued

```
gccgccggtg cggtggacga gggtctggaa tagcgggtgg cccacgagct cctcggcgac    840
gaggtaccgg cggcgcgact tgccgacgta gaccgggtgg aggcccttgg gcacctcgtc    900
cgcgccgtgg aacgaggcgc agtgcgcgtc gccggaggtg cgccgtcgt gggctgatga     960 tggcgacggg gcgcgggaga cgatgcggct cgacgagtgc cacctcttga tcatgcaccg   1020
ga                                                                  1022
```

<210> SEQ ID NO 34
<211> LENGTH: 27
<212> TYPE: DNA
<213> ORGANISM: Artificial sequence
<220> FEATURE:
<223> OTHER INFORMATION: primer

<400> SEQUENCE: 34

```
ttcgaaggat ccgctgcagc tatgtgg                                         27
```

<210> SEQ ID NO 35
<211> LENGTH: 27
<212> TYPE: DNA
<213> ORGANISM: Artificial sequence
<220> FEATURE:
<223> OTHER INFORMATION: primer

<400> SEQUENCE: 35

```
ttctgttcag tgtagcccgg ggtcgac                                         27
```

<210> SEQ ID NO 36
<211> LENGTH: 350
<212> TYPE: DNA
<213> ORGANISM: Zea mays

<400> SEQUENCE: 36

```
gctgcagcta tgtggcgagc aagggccact gcgcggtgta cacggccgac ggggcacggt     60
tcgaggtgcc gctggcgtgc cttagcaccc cggtcttcgg ggagctccta caaatgtcac    120
aggaggagtt cggcttcacg ggcggcgatg gcaggatcac gctgccctgc gacgcggcga    180
tcatggagta cgccatgtgt ttgctcagga gaggagcctc tgctgagcta gagcaggcgt    240
tccttagcac catggccatg tcatgccact gtgccagcca catggcgccg tatgttggac    300
gagctcacga gccagacagc agattgttgt ttagtttctg ttcagtgtag                350
```

<210> SEQ ID NO 37
<211> LENGTH: 350
<212> TYPE: DNA
<213> ORGANISM: Zea mays

<400> SEQUENCE: 37

```
ctacactgaa cagaaactaa acaacaatct gctgtctggc tcgtgagctc gtccaacata     60
cggcgccatg tggctggcac agtggcatga catggccatg gtgctaagga acgcctgctc    120
tagctcagca gaggctcctc tcctgagcaa acacatggcg tactccatga tcgccgcgtc    180
gcagggcagc gtgatcctgc catcgccgcc cgtgaagccg aactcctcct gtgacatttg    240
taggagctcc ccgaagaccg gggtgctaag gcacgccagc ggcacctcga accgtgcccc    300
gtcggccgtg tacaccgcgc agtggcccctt gctcgccaca tagctgcagc                350
```

<210> SEQ ID NO 38
<211> LENGTH: 1122
<212> TYPE: DNA
<213> ORGANISM: Zea mays

<400> SEQUENCE: 38

```
gctgcagcta tgtggcgagc aagggccact gcgcggtgta cacggccgac ggggcacggt      60
tcgaggtgcc gctggcgtgc cttagcaccc cggtcttcgg ggagctccta caaatgtcac     120
aggaggagtt cggcttcacg ggcggcgatg caggatcac gctgccctgc gacgcggcga      180
tcatggagta cgccatgtgt ttgctcagga gaggagcctc tgctgagcta gagcaggcgt     240
tccttagcac catggccatg tcatgccact gtgccagcca catggcgccg tatgttggac     300
gagctcacga gccagacagc agattgttgt ttagtttctg ttcagtgtag cccggggtcg     360
acctgcaggc ggccgcgaat tcactagtga ttctaactaa ctagaggtac agtacacaca     420
catatgtata tatgtatgat gtatcccttc gatcgaaggc atgccttggt cgaataactg     480
agtagtcatt ttattacgtt attttgacaa gtcagtagtt catccatttg tcccattttt     540
tcagctagga agtttggtta cactggcctt ggtctaataa ctgagtagtc attttattac     600
gttgtttcga caagtcagta gctcatccat ctgtcccatt tttttcagct aggaagtttg     660
gttacactgg acttggtcta ataactgagt agtcatttta ttacgttgtt tcgacaagtc     720
attagctcat ccatctgtcc catttttcag ctctaactaa ctagatcccg ggctacactg     780
aacagaaact aaacaacaat ctgctgtctg gctcgtgagc tcgtccaaca tacggcgcca     840
tgtggctggc acagtggcat gacatggcca tggtgctaag gaacgcctgc tctagctcag     900
cagaggctcc tctcctgagc aaacacatgg cgtactccat gatcgccgcg tcgcagggca     960
gcgtgatcct gccatcgccg cccgtgaagc cgaactcctc ctgtgacatt tgtaggagct    1020
ccccgaagac cggggtgcta aggcacgcca gcggcacctc gaaccgtgcc ccgtcggccg    1080
tgtacaccgc gcagtgggcc ttgctcgcca catagctgca gc                       1122
```

<210> SEQ ID NO 39
<211> LENGTH: 36
<212> TYPE: DNA
<213> ORGANISM: Artificial sequence
<220> FEATURE:
<223> OTHER INFORMATION: primer

<400> SEQUENCE: 39

```
ttcgaaggat ccagcgccaa gagacttgtg caaatg                                36
```

<210> SEQ ID NO 40
<211> LENGTH: 27
<212> TYPE: DNA
<213> ORGANISM: Artificial sequence
<220> FEATURE:
<223> OTHER INFORMATION: primer

<400> SEQUENCE: 40

```
gagacgcgtc ggaagcccgg ggtcgac                                          27
```

<210> SEQ ID NO 41
<211> LENGTH: 352
<212> TYPE: DNA
<213> ORGANISM: Zea mays

<400> SEQUENCE: 41

```
agcgccaaga gacttgtgca aatggccaag aagtggcaga ggatggccgc cacggcaagg      60
aggcggatcg cactggcgcc gccggcaaaa ggagccgccg agggatcgtc gccgccgtgc     120
agcacctcgc gtgtagctgt agccggcaag ggccactgcg tggtgtactc ggcggacggc     180
```

```
aggcggttcg aggtcccgct gccgtacctc gacaccgccg tcttcggcgt gctcctcggc    240
atgtcgcggg aggagttcgg gttcgccggt ggcgacggca ggatcacggt gccctgtgac    300
gccgccgtca tggagtacgt catgtgtttg cttcggagag acgcgtcgga ag            352
```

```
<210> SEQ ID NO 42
<211> LENGTH: 352
<212> TYPE: DNA
<213> ORGANISM: Zea mays

<400> SEQUENCE: 42
```

```
cttccgacgc gtctctccga agcaaacaca tgacgtactc catgacggcg gcgtcacagg    60
gcaccgtgat cctgccgtcg ccaccggcga acccgaactc ctcccgcgac atgccgagga    120
gcacgccgaa gacggcggtg tcgaggtacg cagcgggac ctcgaaccgc ctgccgtccg     180
ccgagtacac cacgcagtgg cccttgccgg ctacagctac acgcgaggtg ctgcacggcg    240
gcgacgatcc ctcggcggct ccttttgccg gcggcgccag tgcgatccgc ctccttgccg    300
tggcggccat cctctgccac ttcttggcca tttgcacaag tctcttggcg ct            352
```

```
<210> SEQ ID NO 43
<211> LENGTH: 1126
<212> TYPE: DNA
<213> ORGANISM: Zea mays

<400> SEQUENCE: 43
```

```
agcgccaaga gacttgtgca aatggccaag aagtggcaga ggatggccgc cacggcaagg    60
aggcggatcg cactggcgcc gccggcaaaa ggagccgccg agggatcgtc gccgccgtgc    120
agcacctcgc gtgtagctgt agccggcaag ggccactgcg tggtgtactc ggcggacggc    180
aggcggttcg aggtcccgct gccgtacctc gacaccgccg tcttcggcgt gctcctcggc    240
atgtcgcggg aggagttcgg gttcgccggt ggcgacggca ggatcacggt gccctgtgac    300
gccgccgtca tggagtacgt catgtgtttg cttcggagag acgcgtcgga agcccggggt    360
cgacctgcag gcggccgcga attcactagt gattctaact aactagaggt acagtacaca    420
cacatatgta tatatgtatg atgtatccct tcgatcgaag gcatgccttg gtcgaataac    480
tgagtagtca ttttattacg ttattttgac aagtcagtag ttcatccatt tgtcccattt    540
tttcagctag gaagtttggt tacactggcc ttggtctaat aactgagtag tcattttatt    600
acgttgtttc gacaagtcag tagctcatcc atctgtccca ttttttttcag ctaggaagtt   660 tggttacact ggacttggtc taataactga gtagtcattt tattacgttg tttcgacaag    720
tcattagctc atccatctgt cccatttttc agctctaact aactagatcc cgggcttccg    780
acgcgtctct ccgaagcaaa cacatgacgt actccatgac ggcggcgtca cagggcaccg    840
tgatcctgcc gtcgccaccg gcgaacccga actcctcccg cgacatgccg aggagcacgc    900
cgaagacggc ggtgtcgagg tacgcagcgg gacctcgaa ccgcctgccg tccgccgagt     960
acaccacgca gtggcccttg ccggctacag ctacacgcga ggtgctgcac ggcggcgacg    1020
atccctcggc ggctcctttt gccggcggcg ccagtgcgat ccgcctcctt gccgtggcgg    1080
ccatcctctg ccacttcttg gccatttgca caagtctctt ggcgct                   1126
```

```
<210> SEQ ID NO 44
<211> LENGTH: 400
<212> TYPE: DNA
<213> ORGANISM: Zea mays

<400> SEQUENCE: 44
```

```
ctgcaggcgg ccgcgaattc actagtgatt gtcgacgtgc aaaggtacag tacacacaca       60
tatgtatata tgtatgatgt atcccttcga tcgaaggcat gccttggtcg aataactgag      120
tagtcatttt attacgttat tttgacaagt cagtagttca tccatttgtc ccattttttc      180
agctaggaag tttggttaca ctggccttgg tctaataact gagtagtcat tttattacgt      240
tgtttcgaca agtcagtagc tcatccatct gtcccatttt tttcagctag gaagtttggt      300
tacactggac ttggtctaat aactgagtag tcattttatt acgttgtttc gacaagtcat      360
tagctcatcc atctgtccca tttttcagct ggatcccggg                            400
```

DOWN-REGULATION OF AUXIN RESPONSIVE GENES FOR IMPROVED PLANT PERFORMANCE

FIELD

This disclosure relates generally to the field of molecular biology and the modulation of expression or activity of genes and proteins affecting yield, abiotic stress tolerance and nitrogen utilization efficiency in plants.

BACKGROUND

Grain yield improvements by conventional breeding have nearly reached a plateau in maize. It is natural then to explore some alternative, non-conventional approaches that could be employed to obtain further yield increases. However, to meet the demand of rapid populationin future, greater increases in food production are required. The scale of the increase requires the involvement of new technologies such as transgene-based improvement in agronomic traits. The disclosure can be used for transgene-based improvements of agronomic traits. Therefore, the described gene can be used to improve N use efficiency, increase grain yield and shorten crop maturity.

SUMMARY

The ZmSAUR (a short-lived auxin responsive gene), was down regulated (UBI:ZmSAUR RNAi) in maize. Transgenic plants with down-regulated ZmSAUR expression, produced statistically significant increase of mature ear length, mature ear width and kernel number per ear in T0 phenomics in GS3/GASPE/GASPE background. Therefore, the growth condition also affects the plants productivity. However, in both environments the transgenic plants produced longer ears than the non transgenic control plants. Ear growth is reduced in maize under stressed environments, such as drought and low nitrogen stress or nutrient deficiency, which ultimately contribute to grain yield reduction. The prolificacy of the ZmSAUR transgenic plants offers opportunities to improve yield under the stressed growth environments.

There is a continuing need for modulation of remobilization in plants for manipulating plant development or biomass. This disclosure relates to the creation of novel ZmSAUR downregulation polynucleotide constructs to modulate yield as seed and/or biomass, abiotic stress tolerance, including density tolerance, drought tolerance, low nitrogen stress, nitrogen utilization efficiency and/or other modifications in plants, including novel polynucleotide sequences, expression cassettes, constructs, vectors, plant cells and resultant plants. These and other features of the disclosure will become apparent upon review of the following.

This disclosure provides methods and compositions for modulating yield, drought tolerance, low nitrogen stress and/or nitrogen utilization efficiency in plants as well as speeding up remobilization of nutrients including nitrogen in plants. This disclosure relates to compositions and methods for down-regulating the level and/or activity of ZmSAUR in plants, exemplified by, e.g., SEQ ID NO:1 and/or SEQ ID NO: 3 or 5, including the development of specific RNAi constructs (see, SEQ ID NO: 33, 38 and 43) for creation of plants with improved yield and/or improved abiotic stress tolerance, which may include improved drought tolerance, improved density tolerance, enhanced yield or nitrogen (fertilizer) response in yield under high nitrogen (current commercial hybrids level off of the yield at high fertilizer application), and/or improved NUE (nitrogen utilization efficiency). NUE includes both improved yield in low nitrogen conditions and more efficient nitrogen utilization in normal conditions.

Therefore, in one aspect, the present disclosure relates to an isolated nucleic acid comprising a polynucleotide sequence for use in a down-regulation construct, such as an RNAi vector which modulates ZmSAUR expression. One embodiment of the disclosure is an isolated polynucleotide comprising a nucleotide sequence of SEQ ID NO: 33, 38 or 43, which may optimize interaction with endogenous RNA sequences.

In another aspect, the present disclosure relates to recombinant down-regulation constructs comprising the polynucleotides as described (see, SEQ ID NO: 33, 38 and 43). The down-regulation constructs generally comprise the polynucleotides of SEQ ID NO: 33, 38 or SEQ ID NO: 43 and a promoter operably linked to the same. Additionally, the constructs include several features which result in effective down-regulation of ZmSAUR through RNAi embodiments or facilitate modulation of ZmSAUR expression. One such feature is the inclusion of one or more FLP/FRT sites. Other features include specific elimination of extraneous open reading frames in the hairpin structure, elimination of an open reading frame from the intron of the ubiquitin promoter, alteration of the hairpin to include an AdhI intron and reconfiguration of the construct so that the hairpin cassette and the herbicide-tolerance marker are in tandem orientation. The disclosure also relates to a vector containing the recombinant expression cassette. Further, the vector containing the recombinant expression cassette can facilitate the transcription of the nucleic acid in a host cell. The present disclosure also relates to the host cells able to transcribe a polynucleotide.

In certain embodiments, the present disclosure is directed to a transgenic plant or plant cell containing a polynucleotide comprising a down-regulation construct. In certain embodiments, a plant cell of the disclosure is from a dicot or monocot. Preferred plants containing the polynucleotides include, but are not limited to, maize, soybean, sunflower, *sorghum*, canola, wheat, alfalfa, cotton, rice, barley, tomato and millet. In certain embodiments, the transgenic plant is a maize plant or plant cell. A transgenic seed comprising a transgenic down-regulation construct as described herein is an embodiment. In one embodiment, the plant cell is in a hybrid plant comprising a drought tolerance phenotype and/or a nitrogen utilization efficiency phenotype and/or an improved yield phenotype. In another embodiment, the plant cell is in a plant comprising a sterility phenotype, e.g., a male sterility phenotype. Plants may comprise a combination of such phenotypes. A plant regenerated from a plant cell of the disclosure is also a feature of the disclosure.

Certain embodiments have improved drought tolerance as compared to a control plant. The improved drought tolerance of a plant of the disclosure may reflect physiological aspects such as, but not limited to, (a) a reduction in the production of at least one ZmSAUR-encoding mRNA; (b) a reduction in the production of a ZmSAUR polypeptide; (c) changes in ear tissue development rate; (d) an increase in sink capacity; (e) an increase in plant tissue growth or (f) any combination of (a)-(e), compared to a corresponding control plant. Plants exhibiting improved drought tolerance may also exhibit one or more additional abiotic stress tolerance phenotyoes, such as improved nitrogen utilization efficiency and increased density tolerance.

The disclosure also provides methods for inhibitingshort lived auxin responsive production in a plant and plants produced by such methods. For example, a method of inhibiting short lived auxin responsive production comprises inhibiting the expression of one or more ZmSAUR genes in the plant, wherein the one or more ZmSAUR genes encode one or more ZmSAURs. Multiple methods and/or multiple constructs may be used to downregulate a single ZmSAUR polynucleotide or polypeptide. Multiple ZmSAUR polynucleotides or polypeptides may be downregulated by a single method or by multiple methods; in either case, one or more compositions may be employed.

Methods for modulating drought tolerance in plants are also a feature of the disclosure, as are plants produced by such methods. For example, a method of modulating drought tolerance comprises: (a) selecting at least one ZmSAUR gene to impact, thereby providing at least one desired ZmSAUR gene; (b) introducing a mutant form (e.g., an antisense or sense configuration of at least one ZmSAUR gene or subsequence thereof, an RNA silencing configuration of at least one ZmSAUR gene or subsequence thereof, and the like) of the at least one desired ZmSAUR gene into the plant and (c) expressing the mutant form, thereby modulating drought tolerance in the plant. In certain embodiments, the mutant gene is introduced by *Agrobacterium*-mediated transfer, electroporation, micro-projectile bombardment, a sexual cross or the like.

Detection of expression products is performed either qualitatively (by detecting presence or absence of one or more product of interest) or quantitatively (by monitoring the level of expression of one or more product of interest). In one embodiment, the expression product is an RNA expression product. Aspects of the disclosure optionally include monitoring an expression level of a nucleic acid, polypeptide or chemical, seed production, senesence, dry down rate, etc., in a plant or in a population of plants.

Kits which incorporate one or more of the nucleic acids noted above are also a feature of the disclosure. Such kits can include any of the above noted components and further include, e.g., instructions for use of the components in any of the methods noted herein, packaging materials and/or containers for holding the components. For example, a kit for detection of ZmSAUR expression levels in a plant includes at least one polynucleotide sequence comprising a nucleic acid sequence, where the nucleic acid sequence is, e.g., at least about 70%, at least about 75%, at least about 80%, at least about 85%, at least about 90%, at least about 95%, at least about 99%, about 99.5% or more, identical to SEQ ID NO: 1, 3, or 5 or a subsequence thereof or a complement thereof. In a further embodiment, the kit includes instructional materials for the use of the at least one polynucleotide sequence to modulate drought tolerance in a plant.

DETAILED DESCRIPTION OF THE INVENTION

It is to be understood that the terminology used herein is for the purpose of describing particular embodiments only and is not intended to be limiting. As used in this specification and the appended claims, the singular forms "a", "an" and "the" include plural references unless the content clearly dictates otherwise. Thus, for example, reference to "a cell" includes a combination of two or more cells, and the like.

Unless described otherwise, all technical and scientific terms used herein have the same meaning as commonly understood by one of ordinary skill in the art to which the disclosure pertains. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the disclosure.

The present disclosure now will be described more fully hereinafter with reference to the accompanying drawings and other illustrative non-limiting embodiments.

Many modifications and other embodiments of the disclosure set forth herein are within the scope of the claimed disclosure based on the benefit of the teachings in the present descriptions and the associated drawings. Therefore, it is to be understood that the subject matter described is not to be limited to the specific embodiments disclosed and that modifications and other embodiments are intended to be included within the scope of the appended claims.

The practice of the present disclosure will employ, unless otherwise indicated, conventional techniques of agronomy, botany, microbiology, tissue culture, molecular biology, chemistry, biochemistry and recombinant DNA technology, which are within the skill of the art.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein either by their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present disclosure, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), 0-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32)) can be modified to yield a functionally identical molecule. Accordingly, each silent variation of a nucleic acid is implicit in each described polypeptide sequence and incorporated herein by reference.

As to amino acid sequences, one of skill will recognize that individual substitution, deletion or addition to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, for example, any number of amino acid residues selected from the group of integers consisting of from 1 to 15, such as 1, 2, 3, 4, 5, 7 or 10, can be so altered. Conservatively modified variants typically provide biological activity similar to that of the unmodified polypeptide sequence from which they are derived. For example, substrate specificity, enzyme activity or ligand/receptor binding is generally at least 30%, 40%, 50%, 60%, 70%, 80% or 90%, preferably 60-90% of the binding of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V) and
6) Phenylalanine (F), Tyrosine (Y), Tryptophan (W).

See also, Creighton, *Proteins*, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as does the original object polynucleotide and where the hybridization conditions include a wash step in 0.1×SSC and 0.1% sodium dodecyl sulfate at 65° C. Generally, additional sequence or sequences do not materially affect the basic and novel characteristics of the claimed disclosure. For example, in an embodiment, additional sequences may be included at the 5' or 3' end of the hairpin structure without materially affecting the RNA interference function of the construct.

The term "construct" is used to refer generally to an artificial combination of polynucleotide sequences, i.e., a combination which does not occur in nature, normally comprising one or more regulatory elements and one or more coding sequences. The term may include reference to expression cassettes and/or vector sequences, as is appropriate for the context.

A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma* capricolum (Yamao, et al., (1985) *Proc. Natl. Acad. Sci. USA* 82:2306-9) or the ciliate Macronucleus, may be used when the nucleic acid is expressed using these organisms.

When the nucleic acid is prepared or altered synthetically, advantage can be taken of known codon preferences of the intended host in which the nucleic acid is to be expressed. For example, although nucleic acid sequences may be expressed in both monocotyledonous and dicotyledonous plant species, sequences can be modified to account for the specific codon preferences and GC content preferences of monocotyledonous plants or dicotyledonous plants (see, Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

By "flowering stress" is meant that water is withheld from plants such that drought stress occurs at or around the time of anthesis.

By "grain fill stress" is meant that water is withheld from plants such that drought stress occurs during the time when seeds are accumulating storage products (carbohydrates, protein and/or oil).

By "rain-fed conditions" is meant that water is neither deliberately withheld nor artificially supplemented.

By "well-watered conditions" is meant that water available to the plant is generally adequate for optimum growth.

Drought stress conditions for maize may be controlled to result in a targeted yield reduction. For example, a 20%, 30%, 40%, 50%, 60%, 70% or greater reduction in yield of control plants can be accomplished by providing measured amounts of water during specific phases of plant development.

As used herein, "heterologous" in reference to a nucleic acid is a nucleic acid that originates from a foreign species, or, if from the same species, is substantially modified from its native form in composition and/or genomic locus by deliberate human intervention.

For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell which comprises a heterologous nucleic acid sequence of the disclosure. Host cells may be prokaryotic cells such as *E. coli* or eukaryotic cells such as yeast, insect, plant, amphibian or mammalian cells. Preferably, host cells are monocotyledonous or dicotyledonous plant cells, including but not limited to maize, *sorghum*, sunflower, soybean, wheat, alfalfa, rice, cotton, canola, barley, millet, sugarcane, turfgrass and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "down-regulate" and its forms, e.g. down-regulation, refers to a reduction which may be partial or complete. For example, down-regulation of a ZmSAUR polynucleotide in a plant or cell encompasses a reduction in expression to a level that is 99%, 95%, 90%, 85%, 80%, 75%, 70%, 65%, 60%, 55%, 50%, 45%, 40%, 35%, 30%, 25%, 20%, 15%, 10%, 5% or 0% of the expression level of the corresponding ZmSAUR polynucleotide in a control plant or cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The term "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids which are "isolated", as defined herein, are also referred to as "heterologous" nucleic acids.

As used herein the term "modulation of ZmSAUR activity" shall be interpreted to mean any change in a ZmSAUR biological activity, which can include an altered level of ZmSAUR present in a plant cell, altered efficacy of the enzyme or any other means which affects one or more of the biological properties of ZmSAUR. Accordingly, "inhibition of ZmSAUR activity" encompasses a reduction in the efficacy of the gene or a reduction in the level of ZmSAUR present in a plant cell, for example, due to a reduction in the expression of a ZmSAUR gene.

In other embodiments, expression of a downregulation construct described herein could modulate other steps along the auxin response pathway to improve plant yield or abiotic stress tolerance of a plant. In any event, the disclosure is directed to increasing plant yield in optimum conditions, as well as improving performance under abiotic stress conditions, by modulating expression of a ZmSAUR gene.

The term "nitrogen utilization efficiency" (NUE) refers to physiological processes of uptake and/or assimilation of nitrogen and/or the subsequent remobilization and reutilization of accumulated nitrogen reserves. Improved NUE refers to enhancement of these processes relative to a control plant. Plants in which NUE is improved may be more productive than control plants under comparable conditions of ample nitrogen availability and/or may maintain productivity under significantly reduced nitrogen availability. Improving NUE, particularly in maize, would increase harvestable yield per unit of input nitrogen fertilizer, both in developing nations where access to nitrogen fertilizer is limited and in developed nations where the level of nitrogen use is high. Improved NUE reduces on-farm input costs, decreases dependence on the non-renewable energy sources required for nitrogen fertilizer production and diminishes the environmental impact of nitrogen fertilizer manufacturing and agricultural use. Improved NUE may be reflected in one or more attributes such as increased biomass, increased grain yield, increased harvest index, increased photosynthetic rates and increased tolerance to biotic or abiotic stress. These attributes may reflect or result in changes including a modulation of root development, shoot and leaf development and/or reproductive tissue development. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion. Furthermore, higher root biomass production may affect production of compounds synthesized by root cells or transgenic root cells or cell cultures of said transgenic root cells. Methods of measuring developmental alterations in the root system are known in the art. See, for example, US Patent Application Publication Number 2003/0074698 and Werner, et al., (2001) PNAS 18:10487-10492, both of which are herein incorporated by reference.

Reducing activity of at least one ZmSAUR in a plant can improve the plant growth characteristics of the plant. Such plants may exhibit maintenance of productivity with significantly less nitrogen fertilizer input and/or exhibit enhanced uptake and assimilation of nitrogen fertilizer and/or exhibit altered remobilization and reutilization of accumulated nitrogen reserves or exhibit any combination of such characteristics. In addition to an overall increase in yield, the improvement of nitrogen stress tolerance through the inhibition of ZmSAUR can also result in increased root mass and/or length, increased ear, leaf, seed and/or endosperm size and/or improved standability. Accordingly, in some embodiments, the methods further comprise growing said plants under nitrogen limiting conditions and optionally selecting those plants exhibiting greater tolerance to the low nitrogen levels.

Further, methods and compositions are provided for improving yield under abiotic stress, which include evaluating the environmental conditions of an area of cultivation for abiotic stressors (e.g., low nitrogen levels in the soil), which in some embodiments is due to reduced activity of at least one ZmSAUR, in stressful environments.

The term "low nitrogen conditions" or "nitrogen limiting conditions" as used herein shall be interpreted to mean any environmental condition in which plant-available nitrogen is less than would be optimal for expression of maximum yield potential.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, $2^{nd}$ ed., vols. 1-3 and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells in or from seeds, suspension cultures, embryos, meristematic regions, callus tissue, leaves, roots, shoots, gametophytes, sporophytes, pollen and microspores. The class of plants which can be used in the methods of the disclosure is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "yield" may include reference to bushels per acre of a grain crop at harvest, as adjusted for grain moisture (typically 15% for maize, for example) and/or the volume of biomass generated (e.g. for forage crops such as alfalfa, maize for silage and any species grown for biofuel production). Biomass is measured as the weight of harvestable plant material generated.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as do the naturally occurring polynucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and/or other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such as *Agrobacterium* or *Rhizobium*.

The term "ZmSAUR polypeptide" refers to one or more amino acid sequences of a ZmSAUR polynucleotide. The term is also inclusive of fragments, variants, homologs, alleles or precursors (e.g., preproproteins or proproteins) thereof. A "ZmSAUR protein" comprises a ZmSAUR polypeptide.

As used herein "recombinant" includes reference to a cell or vector that has been modified by the introduction of a heterologous nucleic acid or a cell that is derived from a cell so modified and maintains the modification. Thus, for example, recombinant cells express genes that are not found in identical form within the native (non-recombinant) form of the cell or express native genes that are otherwise abnormally expressed, under expressed or not expressed at all, as a result of deliberate human intervention or may have reduced or eliminated expression of a native gene. In certain examples, recombinant cells exhibit reduced expression of one or more targeted genes or a reduced level or activity of a polypeptide of interest, relative to the non-recombinant cell. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The terms "residue" and "amino acid residue" and "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, often 60-90% sequence identity and may have 100% sequence identity (i.e., are complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part 1, chapter 2, "Overview of principles of hybridization and the strategy of nucleic acid probe assays," Elsevier, New York (1993) and *Current Protocols in Molecular Biology*, chapter 2, Ausubel, et al., eds, Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, a segment of a full-length cDNA or gene sequence or the complete cDNA or gene sequence.

As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or more nucleotides. Those of skill in the art understand that to avoid inference of inappropriately high similarity to a reference sequence, a gap penalty is typically introduced and is subtracted from the number of matches.

Methods of alignment of nucleotide and amino acid sequences for comparison are well known in the art, such as the local homology algorithm (BESTFIT) of Smith and Waterman, (1981) *Adv. Appl. Math* 2:482, which may conduct optimal alignment of sequences for comparison; the homology alignment algorithm (GAP) of Needleman and Wunsch, (1970) *J. Mol. Biol.* 48:443-53; the search for similarity method (Tfasta and Fasta) of Pearson and Lipman, (1988) *Proc. Natl. Acad. Sci. USA* 85:2444 and computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package®, Version 8 (available from Genetics Computer Group (GCG® programs, Accelrys, Inc., San Diego, Calif.)). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater. GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, such as at least 50% 60%, 70%, 80%, 90% or 95% sequence identity, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, such as 55%, 60%, 70%, 80%, 90% or 95%.

Another indication that nucleotide sequences are substantially identical is that two molecules hybridize to each other under stringent conditions. The degeneracy of the genetic code allows for many nucleic acid substitutions that lead to variety in the nucleotide sequence that code for the same amino acid, hence it is possible that two DNA sequences could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

The terms "substantial identity" in the context of a peptide indicates that a peptide comprises a sequence with between 55-100% sequence identity to a reference sequence, such as 55%, 60%, 70%, 80%, 85%, 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above except that residue positions which are not identical may differ by conservative amino acid changes.

Construction of Nucleic Acids

The isolated nucleic acids can be made using: (a) standard recombinant methods, (b) synthetic techniques or (c) combinations thereof. In some embodiments, the polynucleotides will be cloned, amplified or otherwise constructed from plants, fungi or bacteria.

A nucleic acid, excluding the polynucleotide sequence, is optionally a vector, adapter or linker for cloning and/or expression of a polynucleotide. Additional sequences may be added to such cloning and/or expression sequences to optimize their function in cloning and/or expression, to aid in isolation of the polynucleotide or to improve the introduction of the polynucleotide into a cell. For example one may use recombination sites, such as FRT sites, for creation and isolation of the polynucleotides of the disclosure, as disclosed in US Patent Application Publication Number 2008/0202505. Examples of recombination sites are known in the art and include FRT sites (See, for example, Schlake and Bode, (1994) *Biochemistry* 33:12746-12751; Huang, et al., (1991) *Nucleic Acids Research* 19:443-448; Sadowski, (1995) In Progress in Nucleic Acid Research and Molecular Biology vol. 51, pp. 53-91; Cox, (1989) In Mobile DNA, Berg and Howe, (eds) American Society of Microbiology, Washington D.C., pp. 116-670; Umlauf and Cox, (1988) *The EMBO Journal* 7:1845-1852; Buchholz, et al., (1996) *Nucleic Acids Research* 24:3118-3119; Kilby, et al., (1993) *Trends Genet.* 9:413-421; Rossant and Geagy, (1995) *Nat. Med.* 1:592-594; Albert, et al., (1995) *The Plant Journal* 7:649-659; Bayley, et al., (1992) *Plant Mol. Biol.* 18:353-361; Odell, et al., (1990) *Mol. Gen. Genet.* 223:369-378 and Dale and Ow, (1991) *Proc. Natl. Acad. Sci. USA* 88:10558-105620, all of which are herein incorporated by reference.); Lox (Albert, et al., (1995) *Plant J.* 7:649-659; Qui, et al., (1994) *Proc. Natl. Acad. Sci. USA* 91:1706-1710; Stuurman, et al., (1996) *Plant Mol. Biol.* 32:901-913; Odell, et al., (1990) *Mol. Gen. Gevet.* 223:369-378; Dale, et al., (1990) *Gene* 91:79-85 and Bayley, et al., (1992) *Plant Mol. Biol.* 18:353-361; Vega, et al., (2008) *Plant Mol. Biol.* 66(6):587-598).

Site-specific recombinases like FLP cleave and religate DNA at specific target sequences, resulting in a precisely defined recombination between two identical sites. To function, the system needs the recombination sites and the recombinase. No auxiliary factors are needed. Thus, the entire system can be inserted into and function in plant cells. Engineering FLP/FRT sites within, or adjacent to, the hairpin structure may facilitate excision of selectable markers and other vector backbone sequence from a host cell.

Use of cloning vectors, expression vectors, adapters and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMCIneo, pOG44, pOG45, pFRTβGAL, pNEOβGAL, pRS403, pRS404, pRS405, pRS406, pRS413, pRS414, pRS415, pRS416, lambda MOSSIox and lambda MOSEIox. Optional vectors for the present disclosure, include but are not limited to, lambda ZAP II and pGEX. For a description of various nucleic acids see, e.g., Stratagene Cloning Systems, Catalogs 1995, 1996, 1997 (La Jolla, Calif.) and Amersham Life Sciences, Inc, Catalog '97 (Arlington Heights, Ill.).

Synthetic Methods for Constructing Nucleic Acids

The isolated nucleic acids can also be prepared by direct chemical synthesis as known in the art. Chemical synthesis generally produces a single stranded oligonucleotide. This may be converted into double stranded DNA by hybridization with a complementary sequence or by polymerization with a DNA polymerase using the single strand as a template. Longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present disclosure provides 5' and/or 3' UTR regions for modulation of translation of heterologous coding sequences.

Further, the polypeptide-encoding segments of the polynucleotides can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides can be analyzed statistically using commercially available software packages such as "Codon Preference" available from the University of Wisconsin Genetics Computer Group. See, Devereaux, et al., (1984) *Nucleic Acids Res.* 12:387-395) or MacVector 4.1 (Eastman Kodak Co., New Haven, Conn.). The number of polynucleotides (3 nucleotides per amino acid) that can be used to determine a codon usage frequency can be any integer from 3 to the number of polynucleotides tested. Optionally, the polynucleotides will be full-length sequences. An exemplary number of sequences for statistical analysis can be at least 1, 5, 10, 20, 50 or 100.

Recombinant Expression Cassettes

The present disclosure further provides recombinant expression cassettes comprising a nucleic acid. A recombinant expression cassette will typically comprise a polynucleotide operably linked to transcriptional initiation regulatory sequences which will direct the transcription of the polynucleotide in the intended host cell, such as tissues of a transformed plant.

For example, plant expression vectors may include: (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/preferred expression), a transcription initiation start site, a ribosome binding site, an RNA processing signal, a transcription termination site and/or a polyadenylation signal.

A plant promoter fragment can be employed which will direct expression of a polynucleotide in all, or nearly all, tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231: 276-85 and Atanassvoa, et al., (1992) *Plant Journal* 2(3): 291-300); ALS promoter, as described in PCT Application Number WO 1996/30530 and other transcription initiation regions from various plant genes known to those of skill in the art.

Tissue preferred, cell type preferred, developmentally regulated and inducible promoters are examples of "non-constitutive" promoters.

Tissue-preferred promoters can be utilized to target expression within a particular plant tissue. By "tissue-preferred" is intended to mean that expression is predominantly in a particular tissue, albeit not necessarily exclusively in that tissue. Examples include promoters that preferentially initiate transcription in leaves, roots, seeds, endosperm, fibers, xylem vessels, tracheids or sclerenchyma. Certain tissue-preferred promoters may drive expression only in photosynthetic ("green") tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 255(3):337-353; Russell, et al., (1997) *Transgenic Res.* 6(2):157-168; Rinehart, et al., (1996) *Plant Physiol.* 112(3):1331-1351; Van Camp, et al., (1996) *Plant Physiol.* 112(2):525-535; Canevascini, et al., (1996) *Plant Physiol.* 112(2):513-525; Yamamoto, et al., (1995) *Plant Cell Physiol.* 35(5):773-778; Lam, (1995) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590; the maize glb1 promoter (GenBank L22344) and Guevara-Garcia, et al., (1993) *Plant J.* 5(3):595-505. Such promoters can be modified, if necessary, for weak expression. See, also, US Patent Application Number 2003/0074698, herein incorporated by reference.

Shoot-preferred promoters include, shoot meristem-preferred promoters such as promoters disclosed in Weigal, et al., (1992) *Cell* 69:853-859; Accession Number AJ131822; Accession Number Z71981; Accession Number AF059870, the ZAP promoter (U.S. patent application Ser. No. 10/387, 937), the maize tb1 promoter (Wang, et al., (1999) *Nature* 398:236-239 and shoot-preferred promoters disclosed in McAvoy, et al., (2003) *Acta Hort.* (ISHS) 625:379-385.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 15(3):533-553 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-651; Leach and Aoyagi, (1991) *Plant Science* (Limerick) 79(1):69-76); Teeri, et al., (1989) *EMBO J.* 8(2):353-350. Additional root-preferred promoters include the VfENOD-GRP3 gene promoter (Kuster, et al., (1995) *Plant Mol. Biol.* 29(5):759-772); rolB promoter (Capana, et al., (1995) *Plant Mol. Biol.* 25(5):681-691 and the CRWAQ81 root-preferred promoter with the ADH first intron (U.S. Pat. No. 7,411,112). See also, U.S. Pat. Nos. 5,837,876; 5,750,386; 5,633,363; 5,559,252; 5,501,836; 5,110,732 and 5,023,179.

A "cell type"-specific or cell type-preferred promoter primarily drives expression in certain cell types in one or more organs, for example, vascular cells in roots or leaves or mesophyll cells. A mesophyllic cell preferred promoter includes, but is not limited to, known phosphoenopyruvate decarboxylase (PEPC) promoters or putative PEPC promoters from any number of species, for example, *Zea mays, Oryza sativa, Arabidopsis thaliana, Glycine max* or *Sorghum bicolor*. Examples include *Zea mays* PEPC of GenBank Accession Number gi:116268332_HTG AC190686 and gCAT GSS composite sequence; *Oryza sativa* PEPC of GenBank Accession Number gi|20804452|dbj|AP003052.3|; *Arabidopsis thaliana* PEPC of GenBank Accession Number gi|5541653|dbj|AP000370.1|AP000370; gi:7769847 or gi|20198070|gb|AC007087.7; *Glycine max* (GSS contigs) or *Sorghum bicolor* (JGI assembly scaffold_832, 89230 bp., JGI assembly scaffold_1632, (1997) *Plant J.* 12(2):255-265;

Kwon, et al., (1995) *Plant Physiol.* 105:357-67; Yamamoto, et al., (1995) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:5732; Mitra, et al., (1995) *Plant Molecular Biology* 26:35-93; Kayaya, et al., (1995) *Molecular and General Genetics* 258:668-675 and Matsuoka, et al., (1993) *Proc. Natl. Acad. Sci. USA* 90(20):9586-9590.

The plant promoter may be under more precise environmental control, e.g., the promoter may initiate transcription of an operably-linked gene in response to an external stimulus. Such promoters are referred to here as "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress; the Hsp70 promoter, which is inducible by heat stress; the PPDK promoter, which is inducible by light and abiotic-stress-inducible promoters rab17 (Vilardell, et al., (1991) *Plant Mol. Biol.* 17(5):985-993); rd29a (Yamaguchi-Shinozaki, et al., (1993) *Mol. Gen. Genet.* 236:331-340) and KT250 (US Patent Publication Number 2009/0229014); see also, US Patent Publication Number 2004/0123347.

A developmentally regulated promoter may have both a temporal and a spatial limitation, for example, a promoter that drives expression in specific tissue types during pollen development or during inflorescence development. See, e.g., US Patent Publication Numbers 2007/0234444 and 2009/0094713. Another example is a senescence regulated promoter, such as SAM22 (Crowell, et al., (1992) *Plant Mol. Biol.* 18:559-566); see also, U.S. Pat. No. 5,589,052.

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, a polyadenylation region is often included at the 3'-end of a polynucleotide coding region. The polyadenylation region can be derived from a variety of plant genes or from T-DNA. The sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence or the partial coding sequence to increase the amount of the mature message that accumulates in the cytosol; for example, the maize Adh1 and Bz1 introns (Callis, et al., (1987) *Genes Dev.* 1:1183-1200). Inclusion of a spliceable intron in the transcription unit in expression constructs has been shown to increase gene expression at both the mRNA and protein levels (if applicable) up to 1000-fold (Buchman and Berg, (1988) *Mol. Cell Biol.* 8:4395-4405). Such intron enhancement of gene expression is typically greatest when placed near the 5' end of the transcription unit. For a review, see Simpson and Filipowicz, (1996) *Plant Mol. Biol.* 32:1-41.

Plant signal sequences include, but are not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell*, 2:301-13); signal peptides which cause proteins to be secreted, such as that of PRIb (Lind, et al., (1992) *Plant Mol. Biol.* 18:47-53) or barley alpha amylase (BAA) (Rahmatullah, et al., (1989) *Plant Mol. Biol.* 12:119) or signal peptides which target proteins to the plastids such as that of rapeseed enoyl-Acp reductase (Verwaert, et al., (1994) *Plant Mol. Biol.* 26:189-202).

A vector comprising the sequences of a polynucleotide of the present disclosure will typically comprise a marker gene which confers a selectable phenotype on plant cells. The selectable marker gene may encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Also useful are genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene) or other such genes known in the art. The bar gene encodes resistance to the herbicide basta and the ALS gene encodes resistance to the herbicide chlorsulfuron. Also useful are genes encoding resistance to glyphosate; see, for example, U.S. Pat. Nos. 7,462,481; 7,531,339; 7,405,075; 7,666,644; 7,622,641 and 7,714,188. Typical vectors useful for expression of genes in higher plants are well known in the art and include vectors derived from the tumor-inducing (Ti) plasmid of *Agrobacterium tumefaciens* described by Rogers, et al., (1987), *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA*, 86:8402-6. Another useful vector herein is plasmid pBI101.2, available from CLONTECH Laboratories, Inc. (Palo Alto, Calif.).

Expression of Sequences in Host Cells

One may express a polynucleotide in a recombinantly engineered cell such as bacteria, yeast, insect or preferably plant cell. The cell produces the polynucleotide in a non-natural condition (e.g., altered in quantity, composition, location and/or time), because it has been genetically altered through human intervention to do so.

It is expected that those of skill in the art are knowledgeable in the numerous expression systems available for expression of a polynucleotide. No attempt will be made to describe in detail all the various methods known for expression in prokaryotes or eukaryotes.

In brief summary, the expression of isolated polynucleotides will typically be achieved by operably linking, for example, the DNA or cDNA to a promoter, followed by incorporation into an expression vector. The vector can be suitable for replication and integration in either prokaryotes or eukaryotes. Typical expression vectors contain transcription and translation terminators, initiation sequences and promoters useful for regulation of the expression of the DNA. To obtain high level expression of a cloned gene, it is desirable to construct expression vectors which contain, at the minimum, a promoter such as ubiquitin to direct transcription, a ribosome binding site for translational initiation and a transcription/translation terminator. Constitutive promoters are classified as providing for a range of constitutive expression. Thus, some are weak constitutive promoters and others are strong constitutive promoters. See, for example, U.S. Pat. No. 6,504,083. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level" or about 1/10 transcripts to about 1/100 transcripts to about 1/1,000 transcripts.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein are available using *Bacillus* sp. and *Salmonella* (Palva, et al., (1983) *Gene* 22:229-35; Mosbach, et al., (1983) *Nature* 302:543-5).

Expression in Eukaryotes

A variety of eukaryotic expression systems such as yeast, insect cell lines, plant and mammalian cells are known to those of skill in the art. As explained briefly below, the present disclosure can be expressed in these eukaryotic systems. In some embodiments, transformed/transfected plant cells, as discussed infra, are employed as expression systems for production of the proteins of the instant disclosure.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins can also be ligated to various expression vectors for use in transfecting cell cultures of, for instance, insect or plant origin. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins are available, for instance, from the American Type Culture Collection, P.O. Box 1549, Manassas, Va., USA, 20108.

As with yeast, when plant host cells are employed, polyadenlyation or transcription terminator sequences are typically incorporated into the vector. An example of a terminator sequence is the potato pinII terminator (Keil et al., supra; An et al., supra). Sequences for accurate splicing of the transcript may also be included. An example of a splicing sequence is the VP1 intron from SV40 (Sprague, et al., *J. Virol.* 45:773-81 (1983)).

Plant Transformation Methods

Numerous methods for introducing foreign genes into plants are known and can be used to insert a ZmSAUR polynucleotide into a plant host, including biological and physical plant transformation protocols. See, e.g., Miki, et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant and include chemical transfection methods such as calcium phosphate, microorganism-mediated gene transfer such as *Agrobacterium* (Horsch et al., *Science* 227:1229-31 (1985)), electroporation, micro-injection and biolistic bombardment.

Expression cassettes and vectors and in vitro culture methods for plant cell or tissue transformation and regeneration of plants are known and available. See, e.g., Gruber, et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, e.g., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722) and ballistic particle acceleration (see, for example, Sanford, et al., U.S. Pat. No. 4,945,050; WO 1991/10725 and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. Gamborg and Phillips, Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 1991/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. Chapman, et al., pp. 197-209, Longman, N.Y. (pollen); Kaeppler, et al., (1990) *Plant Cell Reports* 9:415-418 and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

Agrobacterium-Mediated Transformation

A widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, a polynucleotide of interest can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion or via a binary system where the vir gene is present on a separate vector. Such systems, vectors for use therein, and methods of transforming plant cells are described in U.S. Pat. No. 4,658,082; US Patent Application Serial Number 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, including but not limited to soybean, maize, *sorghum*, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae and Chenopodiaceae. Monocot plants can now be transformed with some success. EP Patent Number 604662 B1 discloses a method for transforming monocots using *Agrobacterium*. EP Patent Number 672752 B1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Roots or shoots transformed by inoculation of plant tissue with *A. rhizogenes* or *A. tumefaciens* can be used as a source of plant tissue to regenerate transgenic plants, either via somatic embryogenesis or organogenesis. Alternatively, plant tissue, in the form of an explant, such as cotyledonary tissue or leaf disks, can be inoculated with these vectors and cultured under conditions which promote plant regeneration. Examples of such methods for regenerating plant tissue are known to those of skill in the art.

Direct Gene Transfer

Despite the fact that the host range for *Agrobacterium*-mediated transformation is broad, some major cereal crop species and gymnosperms were initially recalcitrant to this mode of gene transfer. Success and refinements have been reported, both for *Agrobacterium*-mediated transformation and for alternative methods, collectively referred to as direct gene transfer. For example, with respect to rice, see, Kathuria, et al., (2007) *Critical Reviews in Plant Sciences* 26:65-103. With respect to wheat, see, He, (2010) *J. Exp. Bot* 61(6):1567-1581; XiuDao, et al., (2010) *Sci. Agri. Sinica* 43(8):1539-1553; Zale, (2009) *Plant Cell Rep.* 28(6):903-913; Wang, et al., (2009) *Cereal Res. Commun.* 37(1):1-12; Greer, (2009) *New Biotech.* 26(1/2):44-52. With respect to sugar cane, see, van der Vyver, (2010) *Sugar Tech.* 12(1):21-25; Joyce, et al., (2010) *Plant Cell Rep.* 29(2):173-183; Kalunke, et al., (2009) *Sugar Tech.* 11(4):365-369; Gilbert, et al., (2009) *Field Crops Res.* 111(1-2):39-46. With respect to turfgrass, see, Cao, (2006) *Plant Cell*, Tissue, Organ Culture 85(3):307-316.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Reducing the Activity and/or Level of an ZmSAUR Polypeptide

Methods are provided to reduce or eliminate the level or activity of a ZmSAUR polypeptide by transforming a plant cell with an expression cassette that expresses a polynucleotide that reduces the expression of the ZmSAUR polypeptide. The polynucleotide may reduce the expression of the ZmSAUR polypeptide directly, by preventing transcription or translation of the ZmSAUR messenger RNA, or indirectly, by encoding a polypeptide that reduces the transcription or translation of a ZmSAUR gene encoding a ZmSAUR polypeptide. Methods for reducing or eliminating the expression of a gene in a plant are well known in the art and any such method may be used in the present disclosure to reduce the expression of ZmSAUR polypeptide.

The expression of a ZmSAUR polypeptide is reduced if the level of the ZmSAUR polypeptide is less than 100%, 99% 95%, 90%, 85%, 80%, 75%, 70%, 65%, 60%, 55%, 50%, 45%, 40%, 35%, 30%, 25%, 20%, 15%, 10%, 5% or 1% of the level of the same ZmSAUR polypeptide in a control plant. In particular embodiments, the level of the ZmSAUR polypeptide in a modified plant is less than 60%, less than 50%, less than 40%, less than 30%, less than 20%, less than 10%, less than 5% or less than 2% of the level of the same or a related ZmSAUR polypeptide in a control plant. The ZmSAUR polynucleotide expression level and/or polypeptide level and/or enzymatic activity may be reduced such that the reduction is phenotypically sufficient to provide tolerance to drought conditions without a yield penalty occurring under well-watered conditions. The level or activity of one or more ZmSAUR polynucleotides, polypeptides or enzymes may be impacted. The expression level of the ZmSAUR polypeptide may be measured directly, for example, by assaying for the quantity of ZmSAUR polypeptide expressed in the plant cell or plant, or indirectly, for example, by measuring the ZmSAUR or remobilization activity in the plant cell or plant or by measuring the phenotypic changes in the plant. Methods for performing such assays are described elsewhere herein.

In certain embodiments of the disclosure, the activity of the ZmSAUR polypeptide is reduced or eliminated by transforming a plant cell with an expression cassette comprising a polynucleotide encoding a polypeptide that inhibits the activity of a ZmSAUR polypeptide. The activity of a ZmSAUR polypeptide is reduced if the activity of the ZmSAUR polypeptide is less than 100%, 99% 95%, 90%, 85%, 80%, 75%, 70%, 65%, 60%, 55%, 50%, 45%, 40%, 35%, 30%, 25%, 20%, 15%, 10%, 5% or 1% of the activity of the same ZmSAUR polypeptide in a control plant. In particular embodiments, the ZmSAUR activity of the ZmSAUR polypeptide in a modified plant is less than 60%, less than 50%, less than 40%, less than 30%, less than 20%, less than 10% or less than 5% of the ZmSAUR activity of the same polypeptide in a control plant. The ZmSAUR activity of a ZmSAUR polypeptide is "eliminated" according to the disclosure when it is not detectable by the assay methods described elsewhere herein. Methods of determining the alteration of activity of a ZmSAUR polypeptide are described elsewhere herein.

In other embodiments, the activity of a ZmSAUR polypeptide may be reduced or eliminated by disrupting or excising at least a part of the gene encoding the ZmSAUR polypeptide. Mutagenized plants that carry mutations in ZmSAUR genes also result in reduced expression of the ZmSAUR gene and/or reduced activity of the encoded ZmSAUR polypeptide.

Thus, many methods may be used to reduce or eliminate the activity of a ZmSAUR polypeptide. One or more methods may be used to reduce the activity of a single ZmSAUR polypeptide. One or more methods may be used to reduce the activity of multiple ZmSAUR polypeptides.

1. Polynucleotide-Based Methods:

In some embodiments, a plant is transformed with an expression cassette that is capable of expressing a polynucleotide that reduces the expression of a ZmSAUR polypeptide. The term "expression" as used herein refers to the biosynthesis of a gene product, including the transcription and/or translation of said gene product. For example, an expression cassette capable of expressing a polynucleotide that reduces the expression of at least one ZmSAUR polypeptide is an expression cassette capable of producing an RNA molecule that inhibits the transcription and/or translation of at least one ZmSAUR polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that modulate the expression of a ZmSAUR polypeptide are given below.

i. Sense Suppression/Cosuppression

In some embodiments, down-regulation of the expression of a ZmSAUR polypeptide may be accomplished by sense suppression or cosuppression. For cosuppression, an expression cassette is designed to express an RNA molecule corresponding to all or part of a messenger RNA encoding a ZmSAUR polypeptide in the "sense" orientation. Overexpression of the RNA molecule can result in reduced expression of the native gene. Accordingly, multiple plant lines transformed with the cosuppression expression cassette are screened to identify those that show the reduction of ZmSAUR polypeptide expression.

The polynucleotide used for cosuppression may correspond to all or part of the sequence encoding the ZmSAUR polypeptide, all or part of the 5' and/or 3' untranslated region of a ZmSAUR polypeptide transcript or all or part of both the coding sequence and the untranslated regions of a transcript encoding a ZmSAUR polypeptide. In some embodiments where the polynucleotide comprises all or part of the coding region for the ZmSAUR polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the full-length sequence or a fragment or portion of the transcript of the endogenous gene, generally greater than about 65% sequence identity, often greater than about 85% sequence identity, sometimes greater than about 95% sequence identity. See, U.S. Pat. Nos. 5,283,184 and 5,034,323, herein incorporated by reference.

ii. Antisense Suppression

In some embodiments, reduction of the expression of the ZmSAUR polypeptide may be obtained by antisense suppression. For antisense suppression, the expression cassette is designed to express an RNA molecule complementary to all or part of a messenger RNA encoding the ZmSAUR polypeptide. Over expression of the antisense RNA molecule can result in reduced expression of the native gene. Accordingly, multiple plant lines transformed with the antisense suppression expression cassette are screened to identify those that show the optimum down-regulation of ZmSAUR polypeptide expression.

The polynucleotide for use in antisense suppression may correspond to all or part of the complement of the sequence encoding the ZmSAUR polypeptide, all or part of the complement of the 5' and/or 3' untranslated region of the ZmSAUR transcript or all or part of the complement of both the coding sequence and the untranslated regions of a transcript encoding the ZmSAUR polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or more nucleotides may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the disclosure, down-regulation of the expression of a ZmSAUR polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in down-regulation of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the optimum down-regulation of ZmSAUR polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 1999/49029, WO 1999/53050, WO 1999/61631 and WO 2000/49035, each of which is herein incorporated by reference.

iv. Hairpin RNA Interference and Intron-Containing Hairpin RNA Interference

In some embodiments of the disclosure, down-regulation of the expression of a ZmSAUR polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited and an antisense sequence that is fully or partially complementary to the sense sequence. The antisense sequence may be located "upstream" of the sense sequence (i.e., the antisense sequence may be closer to the promoter driving expression of the hpRNA than is the sense sequence.) The base-paired stem region may correspond to a portion of a promoter sequence controlling expression of the gene to be inhibited. Thus, the base-paired stem region of the molecule generally determines the specificity of the RNA interference. The sense sequence and the antisense sequence are generally of similar lengths but may differ in length. Thus, these sequences may be portions or fragments of at least 10, 19, 20, 21, 22, 23, 24, 25, 26, 27, 28, 29, 30, 50, 70, 90, 100, 120, 140, 160, 180, 200, 220, 240, 260, 280, 300, 320, 340, 360, 380, 400, 500, 600, 700, 800 or 900 nucleotides in length or at least 1, 2, 3, 4, 5, 6, 7, 8, 9 or 10 kb in length. The loop region of the expression cassette may vary in length. Thus, the loop region may be at least 50, 80, 100, 200, 300, 400, 500, 600, 700, 800 or 900 nucleotides in length or at least 1, 2, 3, 4, 5, 6, 7, 8, 9 or 10 kb in length.

hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to reduce or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing and this increases the efficiency of interference. In some embodiments, the intron is the Adh1 intron 1. Methods for using ihpRNA interference to inhibit the expression of endogenous plant genes are described, for example, in Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 2002/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon-Mediated Interference

Amplicon expression cassettes comprise a plant-virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ZmSAUR polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,635,805, each of which is herein incorporated by reference.

vi. Ribozymes

In some embodiments, the polynucleotide expressed by the expression cassette is catalytic RNA or has ribozyme activity specific for the messenger RNA of the ZmSAUR polypeptide. Thus, the polynucleotide causes the degradation of the endogenous messenger RNA, resulting in reduced expression of the ZmSAUR polypeptide. This method is described, for example, in U.S. Pat. No. 4,987,071, herein incorporated by reference.

Methods for Modulating Drought Tolerance in a Plant

Methods for modulating drought tolerance in plants are also features of the disclosure. The ability to introduce different degrees of drought tolerance into plants offers flexibility in the use of the described subject matter: for example, introduction of strong drought tolerance for improved grain-filling or for silage in areas with longer or drier growing seasons, versus the introduction of a moderate drought tolerance for silage in agricultural areas with shorter growing seasons. Modulation of drought tolerance of a plant of the disclosure may reflect one or more of the following: (a) a reduction in the production of at least one ZmSAUR-encoding mRNA; (b) a reduction in the production of a ZmSAUR; (c) an increase in remobilization; (d) an increase in ear number and kernel number; (e) an increase in sink capacity or (f) any combination of (a)-(e), compared to a corresponding control plant.

For example, a method of the disclosure can include: (a) selecting at least one ZmSAUR gene to mutate, thereby providing at least one desired ZmSAUR gene; (b) introducing a mutant form of the at least one desired ZmSAUR gene into the plant and (c) expressing the mutant form, thereby modulating remobilization in the plant. Plants produced by such methods are also a feature of the disclosure.

The degree of drought tolerance introduced into a plant can be determined by a number of factors, e.g., which ZmSAUR gene is selected, whether the mutant gene member is present in a heterozygous or homozygous state or by the number of members of this family which are inactivated or by a combination of two or more such factors.

Once the desired ZmSAUR gene is selected, a mutant form of the ZmSAUR gene is introduced into a plant. In certain embodiments, the mutant form is introduced by *Agrobacterium*-mediated transfer, electroporation, microprojectile bombardment, homologous recombination or a sexual cross. In certain embodiments, the mutant form includes, e.g., a heterozygous mutation in the at least one ZmSAUR gene, a homozygous mutation in the at least one ZmSAUR gene or a combination of homozygous mutation and heterozygous mutation if more than one ZmSAUR gene is selected. In another embodiment, the mutant form includes a subsequence of the at least one desired ZmSAUR gene in an antisense, sense or RNA silencing or interference configuration.

Expression of the mutant form of the ZmSAUR gene can be determined in a number of ways. For example, detection of expression products is performed either qualitatively (presence or absence of one or more product of interest) or quantitatively (by monitoring the level of expression of one or more product of interest). In one embodiment, the expression product is an RNA expression product. The disclosure optionally includes monitoring an expression level of a nucleic acid or polypeptide as noted herein for detection of ZmSAUR in a plant or in a population of plants.

Methods for Modulating Density Tolerance in a Plant

In addition to increasing tolerance to drought stress in plants of the disclosure compared to a control plant, the disclosure also enables higher density planting of plants of the disclosure, leading to increased yield per acre of corn. Most of the increased yield per acre of corn over the last century has come from increasing tolerance to density, which is a stress to plants. Methods for modulating plant stress response, e.g., increasing tolerance for density, are also a feature of the disclosure. For example, a method of the disclosure can include: (a) selecting at least one ZmSAUR gene to mutate, thereby providing at least one desired ZmSAUR gene; (b) introducing a mutant form of the at least one desired ZmSAUR gene into the plant and (c) expressing the mutant form, thereby modulating density tolerance in the plant. Plants produced by such methods are also a feature of the disclosure. Thus, plants of the disclosure can be planted at higher density than currently practiced by farmers and produce an increase in yield of seed and/or biomass.

Methods for Modulating Nitrogen Utilization Efficiency in a Plant

In addition to increasing tolerance to drought stress and improving density stress tolerance in plants of the disclosure compared to a control plant, the disclosure also may provide greater nitrogen utilization efficiency. For example, a method of the disclosure can include: (a) selecting at least one ZmSAUR gene to mutate, thereby providing at least one desired ZmSAUR gene; (b) introducing a mutant form of the at least one desired ZmSAUR gene into the plant and (c) expressing the mutant form, thereby modulating NUE in the plant. Plants produced by such methods are also a feature of the disclosure. Plants in which NUE is improved may be more productive than control plants under comparable conditions of ample nitrogen availability and/or may maintain productivity under significantly reduced nitrogen availability. Improved NUE may be reflected in one or more attributes such as increased biomass, increased remobilization, increased grain yield, increased harvest index, increased photosynthetic rates and increased tolerance to biotic or abiotic stress. In particular, improving NUE in maize would increase harvestable yield per unit of input nitrogen fertilizer, both in developing nations where access to nitrogen fertilizer is limited and in developed nations where the level of nitrogen use remains high.

Screening/Characterization of Plants or Plant Cells

Plants can be screened and/or characterized genotypically, biochemically, phenotypically or by a combination of two or more of these methods. For example, plants may be characterized to determine the presence, absence and/or expression level (e.g., amount, modulation, such as a decrease or increase compared to a control cell) of a polynucleotide of the disclosure; the presence, absence, expression and/or enzymatic activity of a polypeptide of the disclosure and/or modulation of drought tolerance, modulation of nitrogen use efficiency, modulation of density tolerance and/or modulation of plant growth.

Phenotypic analysis includes, e.g., analyzing changes in chemical composition, morphology or physiological properties of the plant. For example, phenotypic changes can include, but are not limited to, an increase in drought tolerance, an increase in density tolerance, and an increase in nitrogen use efficiency.

A variety of assays can be used for monitoring drought tolerance and/or NUE. For example, assays include, but are not limited to, visual inspection, monitoring photosynthesis measurements and measuring levels of chlorophyll, DNA, RNA and/or protein content of, e.g., the leaves, under stress and non-stress conditions.

Plant cells useful in the disclosure include, but are not limited to, meristem cells, Type I, Type II and Type III callus, immature embryos and gametic cells such as microspores, pollen, sperm and egg. In certain embodiments, the plant cell of the disclosure is from a dicot or monocot. A plant regenerated from the plant cell(s) of the described subject matter is also a feature of the disclosure.

In one embodiment, the plant cell is in a plant, e.g., a hybrid plant, comprising a drought tolerant phenotype. In another embodiment, the plant cell is in a plant comprising a sterility phenotype, e.g., a male sterility phenotype. Through a series of breeding manipulations, the construct impacting a ZmSAUR gene can be moved from one plant line to another plant line. For example, a hybrid plant can be produced by sexual cross of a plant comprising a modified expression of one or more ZmSAUR genes and a control plant.

Modified plant cells are also a feature of the disclosure. In a first aspect, the disclosure provides for an isolated or recombinant plant cell comprising at least one down-regulation construct capable of inhibiting an endogenous ZmSAUR gene; e.g., a nucleic acid sequence, or complement thereof, comprising, e.g., at least about 70%, at least about 75%, at least about 80%, at least about 85%, at least about 90%, at least about 95%, at least about 99%, about 99.5% or more, sequence identity to the down-regulation expression construct of SEQ ID NO: 33, 38 or 43. The down-regulation of expression or activity of at least one ZmSAUR polynucleotide or protein is compared to a corresponding control plant cell lacking the down-regulation construct. Essentially any plant can be used in the methods and compositions of the disclosure. Such species include, but are not restricted to, members of the families Poaceae (formerly Graminae), including *Zea mays* (corn or maize), rye, triticale, barley, millet, rice, wheat, oats, etc.; Leguminosae, including pea, beans, lentil, peanut, yam bean, cowpeas, velvet beans, soybean, clover, alfalfa, lupine, vetch, lotus, sweet clover, *wisteria*, sweetpea, etc.; Compositae, the largest family of vascular plants, including at least 1,000 genera, including important commercial crops such as sunflower; Rosaciae, including raspberry, apricot, almond, peach, rose, etc.; as well as nut plants, including, walnut, pecan, hazelnut, etc., forest trees (including *Pinus, Quercus, Pseutotsuga, Sequoia, Populus*, etc. and other common crop plants, e.g., cotton, *sorghum*, lawn grasses, tomato, potato, pepper, canola, broccoli, cabbage, etc.

Additional plants, as well as those specified above, include plants from the genera: *Acamptoclados, Achnatherum, Achnella, Acroceras, Aegilops, Aegopgon, Agroelymus, Agrohordeum, Agropogon, Agropyron, Agrositanion, Agrostis, Aira, Allolepis, Alloteropsis, Alopecurus, Amblyopyrum, Ammophila, Ampelodesmos, Amphibromus, Amphicarpum, Amphilophis, Anastrophus, Anatherum, Andropogron, Anemathele, Aneurolepidium, Anisantha, Anthaenantia, Anthephora, Anthochloa, Anthoxanthum, Apera, Apluda, Archtagrostis, Arctophila, Argillochloa, Aristida, Arrhenatherum, Arthraxon, Arthrostylidium, Arundinaria, Arundinella, Arundo, Aspris, Atheropogon, Avena* (e.g., oats), *Avenella, Avenochloa, Avenula, Axonopus, Bambusa, Beckmannia, Blepharidachne, Blepharoneuron, Bothriochloa, Bouteloua, Brachiaria, Brachyelytrum, Brachypo-*

*dium, Briza, Brizopyrum, Bromelica, Bromopsis, Bromus, Buchloe, Bulbilis, Calamagrostis, Calamovilfa, Campulosus, Capriola, Catabrosa, Catapodium, Cathestecum, Cenchropsis, Cenchrus, Centotheca, Ceratochloa, Chaetochloa, Chasmanthium, Chimonobambusa, Chionochloa, Chloris, Chondrosum, Chrysopon, Chusquea, Cinna, Cladoraphis, Coelorachis, Coix, Coleanthus, Colpodium, Coridochloa, Cornucopiae, Cortaderia, Corynephorus, Cottea, Critesion, Crypsis, Ctenium, Cutandia, Cylindropyrum, Cymbopogon, Cynodon, Cynosurus, Cytrococcum, Dactylis, Dactyloctenium, Danthonia, Dasyochloa, Dasyprum, Davyella, Dendrocalamus, Deschampsia, Desmazeria, Deyeuxia, Diarina, Diarrhena, Dichanthelium, Dichanthium, Dichelachne, Diectomus, Digitaria, Dimeria, Dimorpostachys, Dinebra, Diplachne, Dissanthelium, Dissochondrus, Distichlis, Drepanostachyum, Dupoa, Dupontia, Echinochloa, Ectosperma, Ehrharta, Eleusine, Elyhordeum, Elyleymus, Elymordeum, Elymus, Elyonurus, Elysitanion, Elytesion, Elytrigia, Enneapogon, Enteropogon, Epicampes, Eragrostis, Eremochloa, Eremopoa, Eremopyrum, Erianthus, Ericoma, Erichloa, Eriochrysis, Erioneuron, Euchlaena, Euclasta, Eulalia, Eulaliopsis, Eustachys, Fargesia, Festuca, Festulolium, Fingerhuthia, Fluminia, Garnotia, Gastridium, Gaudinia, Gigantochloa, Glyceria, Graphephorum, Gymnopogon, Gynerium, Hackelochloa, Hainardia, Hakonechloa, Haynaldia, Heleochloa, Helictotrichon, Hemarthria, Hesperochloa, Hesperostipa, Heteropogon, Hibanobambusa, Hierochloe, Hilaria, Holcus, Homalocenchrus, Hordeum* (e.g., barley), *Hydrochloa, Hymenachne, Hyparrhenia, Hypogynium, Hystrix, Ichnanthus, Imperata, Indocalamus, Isachne, Ischaemum, Ixophorus, Koeleria, Korycarpus, Lagurus, Lamarckia, Lasiacis, Leersia, Leptochloa, Leptochloopsis, Leptocoryphium, Leptoloma, Leptogon, Lepturus, Lerchenfeldia, Leucopoa, Leymostachys, Leymus, Limnodea, Lithachne, Lolium, Lophochlaena, Lophochloa, Lophopyrum, Ludolfia, Luziola, Lycurus, Lygeum, Maltea, Manisuris, Megastachya, Melica, Melinis, Mibora, Microchloa, Microlaena, Microstegium, Milium, Miscanthus, Mnesithea, Molinia, Monanthochloe, Monerma, Monroa, Muhlenbergia, Nardus, Nassella, Nazia, Neeragrostis, Neoschischkinia, Neostapfia, Neyraudia, Nothoholcus, Olyra, Opizia, Oplismenus, Orcuttia, Oryza* (e.g., rice), *Oryzopsis, Otatea, Oxytenanthera, Panicularia, Panicum, Pappophorum, Parapholis, Pascopyrum, Paspalidium, Paspalum, Pennisetum* (e.g., millet), *Phalaris,* Phalaroides, *Phanopyrum, Pharus, Phippsia, Phleum, Pholiurus, Phragmites, Phyllostachys, Piptatherum, Piptochaetium, Pleioblastus, Pleopogon, Pleuraphis, Pleuropogon, Poa, Podagrostis, Polypogon, Polytrias, Psathyrostachys, Pseudelymus, Pseudoroegneria, Pseudosasa, Ptilagrostis, Puccinellia, Pucciphippsia, Redfieldia, Reimaria, Reimarochloa, Rhaphis, Rhombolytrum, Rhynchelytrum, Roegneria, Rostraria, Rottboellia, Rytilix, Saccharum, Sacciolepis, Sasa, Sasaella, Sasamorpha, Savastana, Schedonnardus, Schismus, Schizachne, Schizachyrium, Schizostachyum, Sclerochloa, Scleropoa, Scleropogon, Scolochloa, Scribneria, Secale* (e.g., rye), *Semiarundinaria, Sesleria, Setaria, Shibataea, Sieglingia, Sinarundinaria, Sinobambusa, Sinocalamus, Sitanion, Sorghastrum, Sorghum, Spartina, Sphenopholis, Spodiopogon, Sporobolus, Stapfia, Steinchisma, Stenotaphrum, Stipa, Stipagrostis, Stiporyzopsis, Swallenia, Syntherisma, Taeniatherum, Terrellia, Terrelymus, Thamnocalamus, Themeda, Thinopyrum, Thuarea, Thysanolaena, Torresia, Torreyochloa, Trachynia, Trachypogon, Tragus, Trichachne, Trichloris, Tricholaena, Trichoneura, Tridens, Triodia, Triplasis, Tripogon, Tripsacum, Trisetobromus, Trisetum, Triticosecale, Triticum* (e.g., wheat), *Tuctoria, Uniola, Urachne, Uralepis, Urochloa, Vahlodea, Valota, Vaseyochloa, Ventenata, Vetiveria, Vilf a, Vulpia, Willkommia, Yushania, Zea* (e.g., corn), *Zizania, Zizaniopsis* and *Zoysia.*

Regeneration of Isolated, Recombinant or Transgenic Plants

Transformed plant cells which are derived by plant transformation techniques and isolated or recombinant plant cells derived therefrom, including those discussed above, can be cultured to regenerate a whole plant which possesses the desired genotype (i.e., comprising a ZmSAUR down-regulation nucleic acid) and/or thus the desired phenotype, e.g., improved NUE and/or drought tolerance phenotype, density tolerant phenotype, etc. The desired cells, which can be identified, e.g., by selection or screening, are cultured in medium that supports regeneration. The cells can then be allowed to mature into plants. For example, such regeneration techniques can rely on manipulation of certain phytohormones in a tissue culture growth medium, typically relying on a biocide and/or herbicide marker which has been introduced into the plant together with the desired nucleotide sequences. Alternatively, cells, tissues or plants can be screened for down-regulation of expression and/or activity of ZmSAUR, reduction in plant hormone production conferred by the ZmSAUR down-regulation nucleic acid sequence, etc. Plant regeneration from cultured protoplasts is described in Evans, et al., (1983) Protoplasts Isolation and Culture, Handbook of Plant Cell Culture, pp 124 176, Macmillan Publishing Company, New York; Davey, (1983) *Protoplasts,* pp. 12-29, Birkhauser, Basal 1983; *Dale,* (1983) *Protoplasts pp.* 31-41, Birkhauser, Basel and Binding (1985) *Regeneration of Plants, Plant Protoplasts* pp 21-73, CRC Press, Boca Raton. Regeneration can also be obtained from plant callus, explants, organs or parts thereof. Such regeneration techniques are described generally in Klee, et al., (1987) *Ann Rev of Plant Phys* 38:467-486. See also, e.g., Payne and Gamborg. For transformation and regeneration of maize see, for example, U.S. Pat. No. 5,736,369.

Plants cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant. Plant regeneration from cultured protoplasts is described in Evans, et al., Protoplasts Isolation and Culture, Handbook of Plant Cell Culture, Macmillilan Publishing Company, New York, pp. 124-176 (1983) and Binding, Regeneration of Plants, Plant Protoplasts, CRC Press, Boca Raton, pp. 21-73 (1985).

The regeneration of plants containing the foreign gene introduced by *Agrobacterium* from leaf explants can be achieved as described by Horsch, et al., (1985) *Science* 227:1229-1231. After transformation with *Agrobacterium,* the explants typically are transferred to selection medium. One of skill will realize that the selection medium depends on the selectable marker that is co-transfected into the explants. In this procedure, transformants are grown in the presence of a selection agent and in a medium that induces the regeneration of shoots in the plant species being transformed as described by Fraley, et al., (1983) *Proc. Nat'l. Acad. Sci. USA,* 80:4803. This procedure typically produces shoots, e.g., within two to four weeks, and these transformant shoots (which are typically about 1-2 cm in length) are then transferred to an appropriate root-inducing medium containing the selective agent and an antibiotic to prevent bacterial growth. Selective pressure is typically maintained in the root and shoot medium.

Typically, the transformants will develop roots in about 1-2 weeks and form plantlets. After the plantlets are about 3-5 cm in height, they are placed in sterile soil in fiber pots. Those of skill in the art will realize that different acclimation procedures are used to obtain transformed plants of different species. For example, after developing a root and shoot, cuttings, as well as somatic embryos of transformed plants, are transferred to medium for establishment of plantlets. For a description of selection and regeneration of transformed plants, see, e.g., Dodds and Roberts, (1995) Experiments in Plant Tissue Culture, 3rd Ed., Cambridge University Press. Transgenic plants may be fertile or sterile.

The regeneration of plants from either single plant protoplasts or various explants is well known in the art. See, for example, Methods for Plant Molecular Biology, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, N.Y. (1994); Corn and Corn Improvement, 3rd edition, Sprague and Dudley, Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed-propagated crops, mature transgenic plants can be self-pollinated to produce a homozygous inbred plant. The inbred plant produces seed containing the newly introduced heterologous nucleic acid. These seeds can be grown to produce plants that would produce the selected phenotype. Mature transgenic plants can also be crossed with other appropriate plants, generally another inbred or hybrid, including, for example, an isogenic untransformed inbred.

Parts obtained from the regenerated plant, such as flowers, seeds, leaves, branches, fruit and the like are included in the disclosure, provided that these parts comprise cells comprising the down-regulation construct or a functional fragment thereof. Progeny and variants and mutants of the regenerated plants are also included within the scope of the disclosure, provided that these plants comprise the down-regulation construct or a functional fragment thereof.

Transgenic plants expressing the selectable marker can be screened for transmission of the down-regulation construct by, for example, standard immunoblot and DNA detection techniques. Transgenic lines are also typically evaluated for levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. In addition, in situ hybridization and immunocytochemistry according to standard protocols can be done using heterologous nucleic acid specific polynucleotide probes to localize sites of expression within transgenic tissue. Generally, a number of transgenic lines are screened for the incorporated nucleic acid to identify and select plants with the most appropriate expression profiles.

Some embodiments comprise a transgenic plant that is homozygous for the added heterologous nucleic acid; i.e., a transgenic plant that contains two added nucleic acid sequences at corresponding loci on each chromosome of a chromosome pair. A homozygous transgenic plant can be obtained by sexually mating (self ing) a heterozygous (aka hemizygous) transgenic plant that contains a single added heterologous nucleic acid, germinating some of the seed produced and analyzing the resulting plants produced for altered expression of a polynucleotide of the present disclosure relative to a control plant. Back-crossing to a parental plant and out-crossing with a non-transgenic plant or with a plant transgenic for the same or another trait or traits are also contemplated.

It is also expected that the transformed plants will be used in traditional breeding programs, including TOPCROSS pollination systems as disclosed in U.S. Pat. No. 5,706,603 and U.S. Pat. No. 5,704,160, the disclosure of each of which is incorporated herein by reference.

In addition to Berger, Ausubel and Sambrook, useful general references for plant cell cloning, culture and regeneration include Jones, (ed) (1995) Plant Gene Transfer and Expression Protocols—Methods in Molecular Biology, Volume 49 Humana Press Towata N.J.; Payne, et al., (1992) Plant Cell and Tissue Culture in Liquid Systems, John Wiley & Sons, Inc. New York, N.Y. (Payne) and Gamborg and Phillips, (eds) (1995) Plant Cell, Tissue and Organ Culture; Fundamental Methods Springer Lab Manual, Springer-Verlag (Berlin Heidelberg New York) (Gamborg). A variety of cell culture media are described in Atlas and Parks, (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St. Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology Bios Scientific Publishers, Oxford, UK.

"Stacking" of Constructs and Traits

In certain embodiments, the nucleic acid sequences of the present disclosure can be used in combination ("stacked") with other polynucleotide sequences of interest in order to create plants with a desired phenotype. The polynucleotides of the present disclosure may be stacked with any gene or combination of genes and the combinations generated can include multiple copies of any one or more of the polynucleotides of interest. Stacking can be performed either through molecular stacking or through a conventional breeding approach. Site-specific iintegration of one or more transgenes at the ZmSAUR locus is also possible. The desired combination may affect one or more traits; that is, certain combinations may be created for modulation of gene expression affecting ZmSAUR activity and/or hormone production. Other combinations may be designed to produce plants with a variety of desired traits, including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802 and 5,703,409); barley high lysine (Williamson, et al., (1987) Eur. J. Biochem. 165:99-106 and WO 1998/20122) and high methionine proteins (Pedersen, et al., (1986) J. Biol. Chem. 261:6279; Kirihara, et al., (1988)

*Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present disclosure can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS and/or glyphosate N-acetyltransferase (GAT) genes; see, for example, U.S. Pat. Nos. 7,462,481; 7,531,339; 7,405,075; 7,666,644; 7,622,641 and 7,714,188) and traits desirable for processing or process products such as high oil (e.g., U.S. Pat. No. 6,232,529); modified oils (e.g., fatty acid desaturase genes (U.S. Pat. No. 5,952,544; WO 1994/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present disclosure with polynucleotides affecting agronomic traits such as male sterility (e.g., see, U.S. Pat. No. 5,583,210), stalk strength, flowering time or transformation technology traits such as cell cycle regulation or gene targeting (e.g. WO 1999/61619; WO 2000/17364; WO 1999/25821), the disclosures of which are herein incorporated by reference.

For example, in addition to a ZmSAUR downregulation expression cassette a stacked combination may include one or more expression cassettes providing one or more of the following: modulation of ABA perception/response targeted to reproductive tissues (e.g., eep1 promoter driving *Arabidopsis* ABI1 mutant; see, US Patent Publication Number 2004/0148654); modulation of cytokinin expression or activity (see, e.g., US Patent Publication Number 2009/0165177 and U.S. Pat. No. 6,992,237); modulation of cis-prenyltransferase expression or activity (see, e.g., U.S. Pat. Nos. 6,645,747 and 7,273,737; modulation of cellulose synthase (see, e.g., U.S. Pat. Nos. 7,214,852 and 7,524,933). In one or more of these stacks, the ZmSAUR downregulation expression cassette may comprise a tissue-preferred promoter (see, e.g., the eep5 promoter disclosed in US Patent Publication Number 2009/0307800 or the eep1 promoter disclosed in US Patent Publication Number 2004/0237147).

These stacked combinations can be created by any method, including but not limited to cross breeding plants by any conventional or TopCross methodology or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

Use in Breeding Methods

The transformed plants of the disclosure may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield and better agronomic quality. With mechanical harvesting of many crops, uniformity of plant characteristics such as germination and stand establishment, growth rate, maturity and plant and ear height is desirable. Traditional plant breeding is an important tool in developing new and improved commercial crops. This disclosure encompasses methods for producing a maize plant by crossing a first parent maize plant with a second parent maize plant wherein one or both of the parent maize plants is a transformed plant displaying a drought tolerance phenotype, a sterility phenotype, a density tolerance phenotype or the like, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of maize hybrids in a maize plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques can be moved into another line using traditional breeding techniques that are well known in the plant breeding arts. For example, a backcrossing approach is commonly used to move a transgene from a transformed maize plant to an elite inbred line and the resulting progeny would then comprise the transgene(s). Also, if an inbred line was used for the transformation, then the transgenic plants could be crossed to a different inbred in order to produce a transgenic hybrid maize plant. As used herein, "crossing" can refer to a simple X by Y cross or the process of backcrossing, depending on the context.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

Kits for Modulating Drought Tolerance or Other Traits

Certain embodiments of the disclosure can optionally be provided to a user as a kit. For example, a kit can contain one or more nucleic acid, polypeptide, antibody, diagnostic nucleic acid or polypeptide, e.g., antibody, probe set, e.g., as a cDNA microarray, one or more vector and/or cell line described herein. Most often, the kit is packaged in a suitable container. The kit typically further comprises one or more additional reagents, e.g., substrates, labels, primers or the like for labeling expression products, tubes and/or other accessories, reagents for collecting samples, buffers, hybridization chambers, cover slips, etc. The kit optionally further comprises an instruction set or user manual detailing preferred methods of using the kit components for discovery or application of gene sets. When used according to the instructions, the kit can be used, e.g., for evaluating expression or polymorphisms in a plant sample, e.g., for evaluating ZmSAUR activity, density resistance potential, sterility, etc. Alternatively, the kit can be used according to instructions for using at least one ZmSAUR polynucleotide sequence to modulate drought tolerance in a plant.

As another example, a kit includes a container containing at least one polynucleotide sequence comprising a nucleic acid sequence, wherein the nucleic acid sequence is, e.g., at least about 70%, at least about 75%, at least about 80%, at least about 85%, at least about 90%, at least about 95%, at least about 99%, about 99.5% or more, identical to SEQ ID NO: 1, 3 or 5 or a subsequence thereof or a complement thereof. The kit optionally also includes instructional materials for the use of the at least one polynucleotide sequence in a plant.

Other Nucleic Acid and Protein Assays

In the context of the disclosure, nucleic acids and/or proteins are manipulated according to well known molecular biology methods. Detailed protocols for numerous such procedures are described in, e.g., in Ausubel, et al., Current Protocols in Molecular Biology (supplemented through 2004) John Wiley & Sons, New York ("Ausubel"); Sambrook, et al., Molecular Cloning—A Laboratory Manual (2nd Ed.), Vol. 1-3, Cold Spring Harbor Laboratory, Cold Spring Harbor, N.Y., (1989) ("Sambrook") and Berger and Kimmel, Guide to Molecular Cloning Techniques, Methods in Enzymology volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification and other RNA polymerase mediated techniques (e.g., NASBA), useful, e.g., for amplifying polynucleotides of the disclosure, are found in Mullis, et al., (1987) U.S. Pat. No. 4,683,202; PCR Protocols A Guide to Methods and Applications (Innis, et al., eds) Academic Press Inc. San Diego, Calif. (1990) ("Innis"); Arnheim and Levinson, (1990) C&EN 36; The Journal Of NIH Research (1991) 3:81; Kwoh, et al., (1989) Proc Natl Acad Sci USA 86:1173; Guatelli, et al., (1990) Proc Natl Acad Sci USA 87:1874; Lomell, et al., (1989) J Clin Chem 35:1826; Landegren, et al., (1988) Science 241:1077; Van Brunt, (1990) Biotechnology 8:291; Wu and Wallace, (1989) Gene 4:560; Barringer, et al., (1990) Gene 89:117 and Sooknanan and Malek, (1995) Biotechnology 13:563. Additional methods, useful for cloning nucleic acids in the context of the disclosure, include Wallace, et al., U.S. Pat. No. 5,426,039. Improved methods of amplifying large nucleic acids by PCR are summarized in Cheng, et al., (1994) Nature 369:684 and the references therein.

Certain polynucleotides of the disclosure can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See, e.g., Caruthers, et al., (1992) Meth Enzymol 211:3. In lieu of synthesizing the desired sequences, essentially any nucleic acid can be custom ordered from any of a variety of commercial sources, such as The Midland Certified Reagent Company (mcrc@oligos.com) (Midland, Tex.), The Great American Gene Company (available on the World Wide Web at genco.com) (Ramona, Calif.), ExpressGen, Inc. (available on the World Wide Web at expressgen.com) (Chicago, Ill.), Operon Technologies, Inc. (available on the World Wide Web at operon.com) (Alameda, Calif.) and many others.

TABLE 1

Sequence Identification.

| SEQ ID NO: | POLYNUCLEOTIDE/POLYPEPTIDE | DESCRIPTION |
| --- | --- | --- |
| 1 | Polynucleotide | ZmSAUR33 CDS |
| 2 | polypeptide | ZmSAUR33 translation |
| 3 | polynucleotide | ZmSAUR52 CDS |
| 4 | polypeptide | ZmSAUR52 translation |
| 5 | polynucleotide | ZmSAUR55 CDS |
| 6 | polypeptide | ZmSAUR55 translation |
| 7 | polynucleotide | Glyma17g05090.1 |
| 8 | polypeptide | Glyma17g05090.1 translation |
| 9 | polynucleotide | Glyma11g10260.1 |
| 10 | polypeptide | Glyma11g10260.1 translation |
| 11 | polynucleotide | Glyma12g02570.1 |
| 12 | polypeptide | Glyma12g02570.1 translation |
| 13 | polynucleotide | Glyma09g08490.1 |
| 14 | polypeptide | Glyma09g08490.1 traslation |
| 15 | polynucleotide | Glyma13g17400.1 |
| 16 | polypeptide | Glyma13g17400.1 translation |
| 17 | polynucleotide | Os08g35110.1 |
| 18 | polypeptide | Os08g35110.1 translation |
| 19 | polynucleotide | Os09g37470.1 |
| 20 | polypeptide | Os09g37470.1 translation |
| 21 | polynucleotide | Os09g37500.1 |
| 22 | polypeptide | Os09g37500.1 translation |
| 23 | polynucleotide | Sb07g022190.1 |
| 24 | polypeptide | Sb07g022190.1 translation |
| 25 | polynucleotide | Sb02g031820.1 |

TABLE 1-continued

Sequence Identification.

| SEQ ID NO: | POLYNUCLEOTIDE/ POLYPEPTIDE | DESCRIPTION |
|---|---|---|
| 26 | polypeptide | Sb02g031820.1 translation |
| 27 | polynucleotide | Sb02g031770.1 |
| 28 | polypeptide | Sb02g031770.1 translation |
| 29 | polynucleotide | ZM-SAUR33 Forward Primer |
| 30 | polynucleotide | ZM-SAUR33 Reverse Primer |
| 31 | polynucleotide | ZM-SAUR33 SenseFragment |
| 32 | polynucleotide | ZM-SAUR33 AntisenseFragment |
| 33 | polynucleotide | ZM-SAUR33 RNAiHairpin |
| 34 | polynucleotide | ZM-SAUR52 Forward Primer |
| 35 | polynucleotide | ZM-SAUR52 Reverse Primer |
| 36 | polynucleotide | ZM-SAUR52 SenseFragment |
| 37 | polynucleotide | ZM-SAUR52 AntisenseFragment |
| 38 | polynucleotide | ZM-SAUR52 RNAiHairpin |
| 39 | polynucleotide | ZM-SAUR55 Forward Primer |
| 40 | polynucleotide | ZM-SAUR55 Reverse Primer |
| 41 | polynucleotide | ZM-SAUR55 SenseFragment |
| 42 | polynucleotide | ZM-SAUR55 AntisenseFragment |
| 43 | polynucleotide | ZM-SAUR55 RNAiHairpin |
| 44 | polynucleotide | ADH1 Intron6 |

EXAMPLES

The following examples are offered to illustrate, but not to limit, the claimed subject matter. Various modifications by persons skilled in the art are to be included within the spirit and purview of this application and scope of the appended claims.

Example 1

Designing the ZmSAUR Hairpin Constructs

To generate repeats of the hairpin, primers were designed for each ZmSAUR genes with SfuI-BamHI on the 5' end and PstI-AgeI on the 3' end.
(SEQ IDNO: 29)>ZM-SAUR33 FORWARD PRIMER

TTCGAAGGATCCTCCGGTGCATGATCAAGAGGTGGC (SEQ IDNO: 30)>ZM-SAUR33 REVERSE PRIMER

TCGTCCTCTTCGAGCCCCGGGGTCGAC (SEQ IDNO: 34)>ZM-SAUR52 FORWARD PRIMER

TTCGAAGGATCCGCTGCAGCTATGTGG (SEQ IDNO: 35)>ZM-SAUR52 REVERSE PRIMER

TTCTGTTCAGTGTAGCCCGGGGTCGAC (SEQ IDNO: 39)>ZM-SAUR55 FORWARD PRIMER

TTCGAAGGATCCAGCGCCAAGAGACTTGTGCAAATG (SEQ IDNO: 40)>ZM-SAUR55 REVERSE PRIMER

GAGACGCGTCGGAAGCCCGGGGTCGAC

DNA fragments were generated by PCR reaction using the above primers and cDNA clones of ZmSAUR genes (SEQ ID NOS: 1, 3 and 5)

To generate the sense strand repeat of the hairpin, PCR fragments were cut with BamHI and PstI restriction enzymes. To generate the anti-sense strand repeat PCR fragments were cut SfuI and AgeI restriction enzymes. The ADH1 INTRON6 DNA fragment was cut with PstI and XmaI enzymes. The sticky ends of XmaI are compatabley with AgeI sites.

The digested fragments (SEQ ID NOS: 31, 32, 36, 37, 41 and 42) were then ligated together to form the RNAi vector and will fold together to create the hairpin. The fragments in the final construct will be a bit shorter than the ones described as these fragments were cut at the designated restriction enzyme sites.

Example 2

ZmSAUR Down-Regulation by Hairpin RNA Expression

As noted previously, plant cells and plants can be modified by introduction of a ZmSAUR polynucleotide sequence configured for RNA silencing or interference. This example describes hairpin RNA expression cassettes for modifying drought tolerance, NUE, seed or biomass yield, density tolerance or other phenotypes, e.g., in maize. As noted previously, down-regulation of ZmSAUR(s), e.g., by hairpin RNA (hpRNA) expression, can result in plants or plant cells having reduced expression (up to and including no detectable expression) of one or more ZmSAURs.

Expression of hpRNA molecules specific for one or more ZmSAUR genes (e.g., ZmSAUR promoters, other untranslated regions or coding regions) in plants can alter phenotypes such as drought tolerance, density tolerance, seed or biomass yield and/or nitrogen use efficiency of the plants, through RNA interference.

An hpRNA construct as described herein is generated by linking a ubiquitin promoter to a portion of the coding sequence of a ZmSAUR gene. Each construct is transformed into maize using *Agrobacterium*-mediated transformation techniques or another known transformation method. Nucleic acid molecules and methods for preparing the constructs and transforming maize are as previously described and known in the art; see, e.g., the sections herein entitled "Plant Transformation Methods," "Other Nucleic Acid and Protein Assays" and the following example "Transformation of Maize".

Expression of hpRNA targeting one or more ZmSAUR genes may result in maize plants that display no detrimental effects in vegetative and reproductive growth. Sequence of a plasmid comprising such an hpRNA construct is provided in SEQ ID NO: 33, 38 or 43.

Example 3

RNA Profiling of Endogenous Expression Pattern

Natural or endogenous expression of ZmSAUR genes has been analyzed by using an RNA profiling database, which consists of RNA expression profiles from a large number of libraries and a broad spectrum of the tissue types. Based upon this RNA profiling database, the expression of the native ZmSAUR genes is mainly located in the maize tassel, ear tissues and roots. The higher expression level of ZmSAUR genes is observed at the base of the developing ear when the floret meristem and florets are initiated. Such a tissue expression pattern preferentially the inflorescence tissues, is consistent with its putative function of affecting the development of the maize ear inflorescence

Example 4

Screening of Gaspe Flint Derived Maize Lines Under Water Limiting Conditions Transgenic plants with GS3/GF3/GF3 background will segregate 1:1 in T1 for a transgenic positive and transgene negative segregants. T1 seeds are sown in a 50% Turface and 50% SB300 soil mixture at a uniform depth of 2" from the surface and a planting density of 8.5" between plants (~72K plants/acre). Each T1 plant is grown in a classic 200 size pot (volume equivalent to 1.7 L) and tagged with a bar code label that contains information about the plant's genetic identity, planting date and greenhouse location. Transgenic plants and their non-transgenic segregants are distinguished using DsRED fluorescence screening or ELISA strip tests that detect the presence of a marker gene linked with a gene of interest.

A split block design with stationary blocks is used to minimize spatial variation. Multiple events are evaluated for each construct, and for each event, 15 transgene positive and 15 transgene negative plants are used. Positives and negatives are completely randomized within each event block. The transgene negative plants from events of the same construct are pooled together and used as the construct null, which represents the control.

Drought stress was applied by delivering a minimal amount of liquid fertilizer daily for an extended period of time. Ear shoots are covered with a shoot bag to prevent pollination and are monitored for 1st day of silk-exertion. Immature (un-pollinated) ears are then harvested at 8 days after initial silking and placed in a shoot-bag or other suitable container, labeled with a bar-code tag containing the sample-identification-number and any other info needed for sampled recognition.

Immature ears are harvested by hand at 8 days after initial silking and a digital image is taken. Digital image analysis of immature ear photographs is conducted using image processing software to extract data. Various image processing operations may be performed, e.g. techniques or algorithms to delineate image pixels associated with the immature ear object of interest from the general image background and\or extraneous debris. Data information can be recorded for each whole or subsection of immature ear objects including, without limitation, object area, minor axis length, major axis length, perimeter, ear color, and/or other information regarding ear size, shape, morphology, location or color. Results are analyzed for statistical significance. Significant increase in immature ear parameters or vegetative parameters indicates increased drought tolerance.

Example 5

Screening of Gaspe Flint Derived Maize Lines Under Nitrogen Limiting Conditions Transgenic plants will contain two or three doses of Gaspe Flint-3 with one dose of GS3 (GS3/(Gaspe-3)2× or GS3/(Gaspe-3)3×) and will segregate 1:1 for a dominant transgene. Transgenic GS3×Gaspe T1 seeds and their respective nulls will be planted in 4-inch pots containing TURFACE®, a commercial potting medium and watered four times each day with 1 mM $KNO_3$ growth medium and with 2 mM (or higher) $KNO_3$ growth medium. After emergence, plants are sampled to determine which are transgenic and which are nulls. At anthesis, plants are harvested and dried in a 70° C. oven for 72 hours and the shoot and ear dry weight determined. Results are analyzed for statistical significance. Expression of a transgene results in plants with improved nitrogen use efficiency in 1 mM $KNO_3$ when compared to a transgenic null. Increase in biomass, greenness and/or ear size at anthesis indicates increased NUE.

Example 6

Nitrogen Use Efficiency (NUE) Assay

Seeds of *Arabidopsis thaliana* (control and transgenic line), ecotype Columbia, are surface sterilized (Sanchez, et al., 2002) and then plated on to Murashige and Skoog (MS) medium containing 0.8% (w/v) Bacto™-Agar (Difco). Plates are incubated for 3 days in darkness at 4° C. to break dormancy (stratification) and transferred thereafter to growth chambers (Conviron, Manitoba, Canada) at a temperature of 20° C. under a 16-hr light/8-hr dark cycle. The average light intensity is 120 ρE/m2/s. Seedlings are grown for 12 days and then transferred to soil based pots. Potted plants are grown on a nutrient-free soil LB2 Metro-Mix® 200 (Scott's Sierra Horticultural Products, Marysville, Ohio, USA) in individual 1.5-in pots (*Arabidopsis* system; Lehle Seeds, Round Rock, Tex., USA) in growth chambers, as described above. Plants are watered with 0.6 or 6.5 mM potassium nitrate in the nutrient solution based on Murashige and Skoog (MS free Nitrogen) medium. The relative humidity is maintained around 70%. Sixteen to eighteen days later, plant shoots are collected for evaluation of biomass and SPAD (chlorophyll) readings.

Example 7

Sucrose Growth Assay

The Columbia line of *Arabidopsis thaliana* is obtained from the *Arabidopsis* Biological Resource Center (Columbus, Ohio). For early analysis (Columbia and T3 transgenic lines), seed are surface-sterilized with 70% ethanol for 5 minutes followed by 40% Clorox® for 5 minutes and rinsed with sterile deionized water. Surface-sterilized seed are sown onto square Petri plates (25 cm) containing 95 mL of sterile medium consisting of 0.5 Murashige and Skoog (1962) salts (Life Technologies) and 4% (w/v) phytagel (Sigma). The medium contains no supplemental sucrose. Sucrose is added to medium in 0.1%, 0.5% and 1.5% concentration. Plates are arranged vertically in plastic racks and placed in a cold room for 3 days at 4° C. to synchronize germination. Racks with cold stratified seed are then transferred into growth chambers (Conviron, Manitoba, Canada) with day and night temperatures of 22 and 20° C., respectively. The average light intensity at the level of the rosette is maintained at 110 mol/m2/secl during a 16-hr light cycle development beginning at removal from the cold room (day 3 after sowing) until the seedlings are harvested on day 14. Images are taken and total fresh weight of root and shoot are measured.

Example 8

Low Nitrogen Seedling Assay Protocol

Seed of transgenic events are separated into transgene and null seed. Two different random assignments of treatments are made to each block of 54 pots arranged 6 rows of 9 columns using 9 replicates of all treatments. In one case null seed of 5 events of the same construct are mixed and used as control for comparison of the 5 positive events in this block, making up 6 treatment combinations in each block. In the second case, 3 transgenic positive treatments and their corresponding nulls are randomly assigned to the 54 pots of the block, making 6 treatment combinations for each block, containing 9 replicates of all treatment combinations. In the first case transgenic parameters are compared to a bulked construct null and in the second case transgenic parameters are compared to the corresponding event null. In cases where there are 10, 15 or 20 events in a construct, the events are assigned in groups of 5 events, the variances calculated for each block of 54 pots but the block null means pooled across blocks before mean comparisons are made.

Two seed of each treatment are planted in 4 inch, square pots containing TURFACE®-MVP on 8 inch, staggered centers and watered four times each day with a solution containing the following nutrients:

| | | | |
|---|---|---|---|
| 1 mM $CaCl_2$ | 2 mM $MgSO_4$ | 0.5 mM $KH_2PO_4$ | 83 ppm Sprint330 |
| 3 mM KCl | 1 mM $KNO_3$ | 1 uM $ZnSO_4$ | 1 uM $MnCl_2$ |
| 3 uM $H_3BO_4$ | 1 uM $MnCl_2$ | 0.1 uM $CuSO_4$ | 0.1 uM $NaMoO_4$ |

After emergence the plants are thinned to one seed per pot. Seedlings are harvested 18 days after planting. At harvest, plants are removed from the pots and the Turface washed from the roots. The roots are separated from the shoot, placed in a paper bag and dried at 70° C. for 70 hr. The dried plant parts (roots and shoots) are weighed and placed in a 50 ml conical tube with approximately 20 5/32 inch steel balls and ground by shaking in a paint shaker. Approximately, 30 mg of the ground tissue is hydrolyzed in 2 ml of 20% $H_2O_2$ and 6M $H_2SO_4$ for 30 minutes at 170° C. After cooling, water is added to 20 ml, mixed thoroughly, and a 50 µl aliquot removed and added to 950 µl 1M $Na_2CO_3$. The ammonia in this solution is used to estimate total reduced plant nitrogen by placing 100 µl of this solution in individual wells of a 96 well plate followed by adding 50 µl of OPA solution. Fluorescence, excitation=360 nM/emission=530 nM, is determined and compared to $NH_4Cl$ standards dissolved in a similar solution and treated with OPA solution.
OPA solution—5 µl Mercaptoethanol+1 ml OPA stock solution
OPA stock—50 mg o-phthadialdehyde (OPA-Sigma #P0657) dissolved in 1.5 ml methanol+4.4 ml 1M Borate buffer pH9.5 (3.09 g $H_3BO_4$+1 g NaOH in 50 ml water)+ 0.55 ml 20% SDS The following parameters are measured and means compared to null mean parameters using a Student's t test: total plant biomass; root biomass; shoot biomass; root/shoot ratio; plant N concentration; total plant N.

Variance is calculated within each block using a nearest neighbor calculation as well as by Analysis of Variance (ANOVA) using a completely random design (CRD) model. An overall treatment effect for each block is calculated using an F statistic by dividing overall block treatment mean square by the overall block error mean square.

Example 9

Transformation of Maize

Biolistics

Polynucleotides contained within a vector can be transformed into embryogenic maize callus by particle bombardment, generally as described by Tomes, et al., Plant Cell, Tissue and Organ Culture: Fundamental Methods, Eds. Gamborg and Phillips, Chapter 8, pgs. 197-213 (1995) and as briefly outlined below. Transgenic maize plants can be produced by bombardment of embryogenically responsive immature embryos with tungsten particles associated with DNA plasmids. The plasmids typically comprise a selectable marker and a structural gene, or a selectable marker and a ZmSAUR downregulation polynucleotide sequence or subsequence, or the like.

Preparation of Particles

Fifteen mg of tungsten particles (General Electric), 0.5 to 1.8µ, preferably 1 to 1.8µ, and most preferably 1µ, are added to 2 ml of concentrated nitric acid. This suspension is sonicated at 0° C. for 20 minutes (Branson Sonifier Model 450, 40% output, constant duty cycle). Tungsten particles are pelleted by centrifugation at 10000 rpm (Biofuge) for one minute and the supernatant is removed. Two milliliters of sterile distilled water are added to the pellet, and brief sonication is used to resuspend the particles. The suspension is pelleted, one milliliter of absolute ethanol is added to the pellet and brief sonication is used to resuspend the particles. Rinsing, pelleting and resuspending of the particles are performed two more times with sterile distilled water and finally the particles are resuspended in two milliliters of sterile distilled water. The particles are subdivided into 250-µl aliquots and stored frozen.

Preparation of Particle-Plasmid DNA Association

The stock of tungsten particles are sonicated briefly in a water bath sonicator (Branson Sonifier Model 450, 20% output, constant duty cycle) and 50 µl is transferred to a microfuge tube. The vectors are typically cis: that is, the selectable marker and the gene (or other polynucleotide sequence) of interest are on the same plasmid.

Plasmid DNA is added to the particles for a final DNA amount of 0.1 to 10 µg in 10 µL total volume and briefly sonicated. Preferably, 10 µg (1 µg/µL in TE buffer) total DNA is used to mix DNA and particles for bombardment. Fifty microliters (50 µL) of sterile aqueous 2.5 M $CaCl_2$ are added and the mixture is briefly sonicated and vortexed. Twenty microliters (20 µL) of sterile aqueous 0.1 M spermidine are added and the mixture is briefly sonicated and vortexed. The mixture is incubated at room temperature for 20 minutes with intermittent brief sonication. The particle suspension is centrifuged and the supernatant is removed. Two hundred fifty microliters (250 µL) of absolute ethanol are added to the pellet, followed by brief sonication. The suspension is pelleted, the supernatant is removed and 60 µl of absolute ethanol are added. The suspension is sonicated briefly before loading the particle-DNA agglomeration onto macrocarriers.

Preparation of Tissue

Immature embryos of maize variety High Type II are the target for particle bombardment-mediated transformation. This genotype is the F1 of two purebred genetic lines, parents A and B, derived from the cross of two known maize inbreds, A188 and B73. Both parents were selected for high competence of somatic embryogenesis, according to Armstrong, et al., (1991) *Maize Genetics Coop. News* 65:92.

Ears from F1 plants are selfed or sibbed and embryos are aseptically dissected from developing caryopses when the scutellum first becomes opaque. This stage occurs about 9 to 13 days post-pollination and most generally about 10 days post-pollination, depending on growth conditions. The embryos are about 0.75 to 1.5 millimeters long. Ears are surface sterilized with 20% to 50% Clorox® for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite® and 8.5 mg/l $AgNO_3$. Chu, et al., (1975) *Sci. Sin.* 18:659; Eriksson, (1965) *Physiol. Plant* 18:976. The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3 to 16 hours, preferably 4 hours, in complete darkness at 28° C. just prior to bombardment with particles associated with plasmid DNA.

To effect particle bombardment of embryos, the particle-DNA agglomerates are accelerated using a DuPont PDS-1000 particle acceleration device. The particle-DNA agglomeration is briefly sonicated and 10 µl are deposited on macrocarriers and the ethanol is allowed to evaporate. The macrocarrier is accelerated onto a stainless-steel stopping screen by the rupture of a polymer diaphragm (rupture disk). Rupture is affected by pressurized helium. The velocity of particle-DNA acceleration is determined based on the rupture disk breaking pressure. Rupture disk pressures of 200 to 1800 psi are used, with 650 to 1100 psi being preferred and about 900 psi being most highly preferred. Multiple disks are used to affect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite®, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from a fraction of the bombarded embryos. Putative transgenic tissue is rescued and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the ZmSAUR and non-ZmSAUR portion of the plasmid. Embryogenic tissue with amplifiable sequence is advanced to plant regeneration.

For regeneration of transgenic plants, embryogenic tissue is subcultured to a medium comprising MS salts and vitamins (Murashige and Skoog, (1962) *Physiol. Plant* 15:473), 100 mg/l myo-inositol, 60 gm/l sucrose, 3 gm/l Gelrite®, 0.5 mg/l zeatin, 1 mg/l indole-3-acetic acid, 26.4 ng/l cis-trans-abscissic acid and 3 mg/l bialaphos in 100×25 mm Petri dishes and is incubated in darkness at 28° C. until the development of well-formed, matured somatic embryos is seen. This requires about 14 days. Well-formed somatic embryos are opaque and cream-colored and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite® in 100×25 mm Petri dishes and incubated under a 16 hour light:8 hour dark photoperiod and 40 meinsteinsm$^{-2}$ sec$^{-1}$ from cool-white fluorescent tubes. After about 7 days, the somatic embryos germinate and produce a well-defined shoot and root. The individual plants are subcultured to germination medium in 125×25 mm glass tubes to allow further plant development. The plants are maintained under a 16 hour light: 8 hour dark photoperiod and 40 meinsteinsm$^{-2}$ sec–1 from cool-white fluorescent tubes. After about 7 days, the plants are well-established and are transplanted to horticultural soil, hardened off and potted into commercial greenhouse soil mixture and grown to sexual maturity in a greenhouse. An elite inbred line is used as a male to pollinate regenerated transgenic plants.

*Agrobacterium*-Mediated

For *Agrobacterium*-mediated transformation, the method of Zhao, et al., may be employed as in PCT Patent Publication Number WO 1998/32326, the contents of which are hereby incorporated by reference. Briefly, immature embryos are isolated from maize and the embryos contacted with a suspension of *Agrobacterium* (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos re cultured on medium containing a selective agent and growing transformed callus is recovered (step 4:

the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants.

Example 10

Expression of Transgenes in Monocots

A plasmid vector is constructed comprising a preferred promoter operably linked to an isolated polynucleotide comprising a ZmSAUR polynucleotide sequence or subsequence. This construct can then be introduced into maize cells by the following procedure.

Immature maize embryos are dissected from developing caryopses derived from crosses of maize lines. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus, consisting of undifferentiated masses of cells with somatic proembryoids and embryoids borne on suspensor structures, proliferates from the scutellum of these immature embryos. The embryogenic callus isolated from the primary explant can be cultured on N6 medium and sub-cultured on this medium every 2 to 3 weeks.

The plasmid p35S/Ac (Hoechst Ag, Frankfurt, Germany) or equivalent may be used in transformation experiments in order to provide for a selectable marker. This plasmid contains the Pat gene (see, EP Patent Publication Number 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and comprises the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton flying disc (Bio-Rad Labs). The particles are then accelerated into the corn tissue with a Biolistic™ PDS-1000/He biolistic particle delivery system (Bio-Rad Instruments, Hercules, Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains glufosinate (2 mg per liter) and lacks casein or proline. The tissue continues to grow slowly on this medium. After an additional 2 weeks the tissue can be transferred to fresh N6 medium containing glufosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Example 11

Expression of Transgenes in Dicots

Soybean embryos are bombarded with a plasmid comprising a preferred promoter operably linked to a heterologous nucleotide sequence comprising a ZmSAUR polynucleotide sequence or subsequence as follows. To induce somatic embryos, cotyledons of 3 to 5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A DuPont Biolistic™ PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette of interest, comprising the preferred promoter and a heterologous ZmSAUR polynucleotide, can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M) and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×5 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Field Trials Under Nitrogen Stress and Normal Nitrogen Conditions

Corn hybrids containing a ZmSAUR down-regulation construct transgene are planted in the field under nitrogen-stress and normal-nitrogen conditions. Under normal nitrogen, a total of 250 lbs nitrogen is applied in the form of urea ammonium nitrate (UAN). Nitrogen stress is achieved through depletion of soil nitrogen reserves by planting corn with no added nitrogen for two years. Soil nitrate reserves are monitored to assess the level of depletion. To achieve the target level of stress, UAN is applied by fertigation or sidedress between V2 and VT growth stages, for a total of 50-150 lbs nitrogen.

Events from the construct are nested together with the null to minimize the spatial effects of field variation. Multiple reps are planted. The seed yield of events containing the transgene is compared to the yield of a transgenic null. Statistical analysis is conducted to assess whether there is a significant improvement in yield compared with the transgenic null, taking into account row and column spatial effects.

Differences in yield, yield components or other agronomic traits between transgenic and non-transgenic plants in reduced-nitrogen fertility plots may indicate improvement in nitrogen utilization efficiency contributed by expression of a transgenic event. Similar comparisons are made in plots supplemented with recommended nitrogen fertility rates. Effective transgenic events may achieve similar yields in the nitrogen-limited and normal nitrogen environments or may perform better than the non-transgenic counterpart in low-nitrogen environments.

In addition, the ZmSAUR transgenic plants have increased sink capacity as result of mature ear length, mature ear width and kernel number per ear production. Realizing the yield potential may be achieved through increasing source strength and nutrient supply by either transgene manipulation or anronomic cultivation. Therefore, the ZmSAUR transgenic may be used to increase yield under high N and fertilizer application, a condition most current commercial hybrids no longer respond to in yield increase, or plateau and are limited by sink capacity. Experiments where higher N levels per plant, or higher photosynthetic activity per plants are created may demonstrate the value of combining ZmSAUR with native germplasm, or other transgenic plants having more source production. The balance between sink size (kernel number/plant) and source size (photosynthetic carbon fixation) may be critical in securing commercial levels of improved yield.

Example 13

Evaluation of Construct for Effect on Yield Components

In order to measure the effect of transgene insertion on the yield components responsible for economic grain yield in maize, hybrid corn in grown under representative field conditions. The component values are measured in order to compare the plant results of the non-transformed plants, and/or wild type hybrids to the same hybrid containing the novel transgene insertion.

Plant seeds are planted in replicated field studies with common plant densities provided for all plots. Nutrient, water, insect control and weed control is provided to encourage good growth during the growing season. At maturity, measurements are performed on 10 sequential plants of the null and transgenic hybrids, including, but not limited to: number of ears, total number of kernels/plant, average weight per kernel. Calculations are performed to determine the total number of kernels produced/acre: kernels/plant× plants/acre, and uield (bu/acre): total kernels/acre×average weight/kernel. Constructs that improve one or more yield components, and/or calculated yield/acre would be deemed as having potential for improved commercial productivity in maize.

Example 14

Variant Sequences

It is also recognized that the level and/or activity of the polypeptide may be modulated by employing a polynucleotide that is not capable of directing, in a transformed plant, the expression of a protein or an RNA. For example, the polynucleotides of the disclosure may be used to design polynucleotide constructs that can be employed in methods for altering or mutating a genomic nucleotide sequence, or its expression, in an organism. Such polynucleotide constructs include, but are not limited to, RNA:DNA vectors, RNA:DNA mutational vectors, RNA:DNA repair vectors, mixed-duplex oligonucleotides, self-complementary RNA: DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984, all of which are herein incorporated by reference. See also, PCT Application Publication Numbers WO 1998/49350, WO 1999/07865, WO 1999/25821 and Beetham, et al., (1999) *Proc. Natl. Acad. Sci. USA* 96:8774-8778, herein incorporated by reference.

The ZmSAUR nucleotide sequences can be used to generate variant nucleotide sequences having the nucleotide sequence of the open reading frame with about 70%, 75%, 80%, 85%, 90% or 95% nucleotide sequence identity when compared to the starting unaltered ORF nucleotide sequence of SEQ ID NO: 1, 3 or 5. These functional variants are generated using a standard codon table. While the nucleotide sequence of the variant is altered, the amino acid sequence encoded by the open reading frame does not change.

Provided in this disclosure are multiple ZmSAUR gene sequences that could be used for RNAi. One gene sequence comprised the 5' of the area used in ZmSAUR and another comprises the gene sequence 3' of that region. Also disclosed is the area between these two regions and the sequence actually used in ZmSAUR that covers the entire gene. These sequences are listed by themselves, as well as in longer (500 bp) fragments that will partially overlap with the area used in ZmSAUR, as optimal length is about 500 bp when designing an RNAi, although a shorter fragment could be used.

Certain embodiments include plants having a transgene comprising a polynucleotide operably linked to a heterologous promoter that drives expression in the plant, wherein expression of the transgene results in modulation of expression of a short lived auxin responsive production polynucleotide and/or polypeptide. Modulation of expression of other genes, including other short lived auxin responsive production genes, may occur as a result of expression of the same transgene or a different transgene. Expression of the transgene may be constitutive or may be directed preferentially to a particular plant cell type or plant tissue type or may be inducible or otherwise controlled. Methods are provided to modulate plant growth and development, particularly plant response to stress, particularly abiotic stress, relative to a control plant, control plant cell or control plant part. The modulated growth or development may be reflected in, for example, higher growth rate, higher yield, altered morphology or appearance and/or an altered response to stress including an improved tolerance to stress. In certain embodiments, the stress is cold, salt or drought. In certain embodiments, yield is increased or maintained during periods of abiotic stress. Yield may be measured, for example, in terms of seed yield, plant biomass yield or recovery of other plant product or products. Seed set may be measured by, for example, seed number, total seed mass, average seed mass or some combination of these or other measures.

While the foregoing subject matter has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications and/or other documents cited in this application are incorporated by reference in their entirety for all purposes to the same extent as if each individual publication, patent, patent application and/or other document were individually indicated to be incorporated by reference for all purposes.

What is claimed is:

1. A maize plant or a maize plant cell comprising an expression cassette effective for reducing expression of at least one endogenous short lived auxin responsive production gene, wherein said expression cassette comprises a promoter that functions in plants operably linked to a nucleic acid configured for RNA silencing or interference, wherein said endogenous short lived auxin responsive production gene encodes a polypeptide that comprises an amino acid sequence that is at least 95% identical to the sequence selected from the group consisting of SEQ ID NOS: 2, 4 and 6.

2. A maize plant regenerated from the plant cell of claim 1, wherein the plant exhibits increased seed yield compared to a control plant.

3. A method of increasing kernel number in a maize plant, the method comprising reducing the expression of one or more ZmSAUR genes in the maize plant, wherein the ZmSAUR genes encode a polypeptide comprising an amino acid sequence selected from the group consisting of SEQ ID NOS: 2, 4 and 6.

* * * * *